United States Patent
Tsukada et al.

(10) Patent No.: US 10,266,636 B2
(45) Date of Patent: Apr. 23, 2019

(54) PROCESS FOR PRODUCING EPISULFIDE COMPOUND FOR OPTICAL MATERIAL, EPISULFIDE-CONTAINING COMPOSITION, AND POLYMERIZABLE COMPOSITION FOR OPTICAL MATERIAL INCLUDING THE SAME COMPOSITION

(71) Applicant: MITSUI CHEMICALS, INC., Minato-ku, Tokyo (JP)

(72) Inventors: Hidetaka Tsukada, Omuta (JP); Masaru Kawaguchi, Omuta (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 104 days.

(21) Appl. No.: 15/124,906

(22) PCT Filed: Mar. 11, 2015

(86) PCT No.: PCT/JP2015/057166
§ 371 (c)(1),
(2) Date: Sep. 9, 2016

(87) PCT Pub. No.: WO2015/137402
PCT Pub. Date: Sep. 17, 2015

(65) Prior Publication Data
US 2017/0015777 A1    Jan. 19, 2017

(30) Foreign Application Priority Data

Mar. 11, 2014 (JP) .................. 2014-047890
Sep. 12, 2014 (JP) .................. 2014-185995

(51) Int. Cl.
| | | |
|---|---|---|
| C08G 18/38 | (2006.01) |
| G02B 1/04 | (2006.01) |
| C08G 18/73 | (2006.01) |
| C08G 18/79 | (2006.01) |
| C08G 18/02 | (2006.01) |
| B29D 11/00 | (2006.01) |
| C08J 5/00 | (2006.01) |
| G02C 7/12 | (2006.01) |
| C07D 331/02 | (2006.01) |
| C08G 18/75 | (2006.01) |
| C08L 75/04 | (2006.01) |
| C08L 81/00 | (2006.01) |

(Continued)

(52) U.S. Cl.
CPC .... *C08G 18/3874* (2013.01); *B29D 11/00009* (2013.01); *B29D 11/00442* (2013.01); *B29D 11/00644* (2013.01); *C07D 331/02* (2013.01); *C08G 18/022* (2013.01); *C08G 18/3876* (2013.01); *C08G 18/73* (2013.01); *C08G 18/753* (2013.01); *C08G 18/758* (2013.01); *C08G 18/792* (2013.01); *C08J 5/00* (2013.01); *G02B 1/04* (2013.01); *G02B 1/041* (2013.01); *G02C 7/12* (2013.01); *B29K 2075/00* (2013.01); *B29K 2105/20* (2013.01); *B29K 2995/0034* (2013.01); *C08J 2375/04* (2013.01); *G02C 2202/16* (2013.01)

(58) Field of Classification Search
CPC .. C08G 18/3874; C08G 18/73; C08G 18/792; C08G 18/022; C08G 18/3876; C08G 18/753; C08G 18/758; G02B 1/04; G02B 1/041; B29D 11/00009; B29D 11/00442; B29D 11/00644; C08J 5/00; C08J 2375/04; G02C 7/12; G02C 2202/16; C07D 331/02; B29K 2075/00; B29K 2105/20; B29K 2995/0034
USPC ........................................................ 428/419
See application file for complete search history.

(56) References Cited

U.S. PATENT DOCUMENTS 6,204,311 B1   3/2001 Morijiri et al.
6,300,464 B2   10/2001 Morijiri et al.
(Continued)

FOREIGN PATENT DOCUMENTS

CN   101490601 A   7/2009
EP   1326095 A1   7/2003
(Continued)

OTHER PUBLICATIONS

Office Action issued by the Korean Patent Office in corresponding Korean Patent Application No. 10-2016-7025972 dated Aug. 10, 2017 (7 pages).
(Continued)

*Primary Examiner* — David T Karst
(74) *Attorney, Agent, or Firm* — Buchanan, Ingersoll & Rooney PC

(57) ABSTRACT

A process for producing an episulfide compound for an optical material of the present invention includes a step of chlorinating glycerin to obtain dichloropropanol; a step of epoxidizing the dichloropropanol to obtain epichlorohydrin; a step of reacting the epichlorohydrin with a sulfating agent to obtain a bis(chlorohydrin) (di)sulfide compound thought a thiol compound; a step of epoxidizing the bis(chlorohydrin) (di)sulfide compound under basic conditions to obtain an epoxy compound; and a step of reacting the epoxy compound with a sulfating agent to obtain an episulfide compound represented by following General Formula (1):

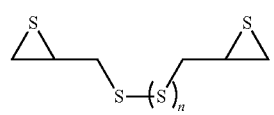

(1)

wherein, in the formula, n represents 0 or 1.

3 Claims, No Drawings

(51) Int. Cl.
*B29K 75/00* (2006.01)
*B29K 105/20* (2006.01)

(56) References Cited

U.S. PATENT DOCUMENTS

| | | | |
|---|---|---|---|
| 6,458,917 | B2 | 10/2002 | Morijiri et al. |
| 6,472,495 | B1 | 10/2002 | Yoshimura et al. |
| 7,091,307 | B2 | 8/2006 | Yoshimura et al. |
| 7,967,434 | B2 | 6/2011 | Miura et al. |
| 8,496,859 | B2 | 7/2013 | Miura et al. |
| 9,234,069 | B2 | 1/2016 | Nakagawa et al. |
| 9,242,947 | B2 | 1/2016 | Aoki et al. |
| 2001/0002413 | A1 | 5/2001 | Morijiri et al. |
| 2002/0019511 | A1 | 2/2002 | Morijiri et al. |
| 2004/0122201 | A1 | 6/2004 | Yoshimura et al. |
| 2006/0149018 | A1 | 7/2006 | Kitahara |
| 2013/0153401 | A1 | 6/2013 | Gilbeau et al. |
| 2013/0184477 | A1 | 7/2013 | Gilbeau |
| 2013/0338330 | A1 | 12/2013 | Nakagawa et al. |
| 2014/0371475 | A1 | 12/2014 | Aoki et al. |
| 2014/0378628 | A1 | 12/2014 | Aoki et al. |
| 2016/0083503 | A1 | 3/2016 | Nakagawa et al. |
| 2016/0090368 | A1 | 3/2016 | Nakagawa et al. |

FOREIGN PATENT DOCUMENTS

| | | |
|---|---|---|
| EP | 2810972 A1 | 12/2014 |
| EP | 3103824 A1 | 12/2016 |
| JP | 11-322930 A | 11/1999 |
| JP | 2000-256435 A | 9/2000 |
| JP | 2001-131257 A | 5/2001 |
| JP | 2001-163874 A | 6/2001 |
| JP | 2002-122701 A | 4/2002 |
| JP | 2002-194083 A | 7/2002 |
| JP | 2003-48883 A | 2/2003 |
| JP | 2003-98301 A | 4/2003 |
| JP | 2004-256746 A | 9/2004 |
| JP | 2005-220162 A | 8/2005 |
| JP | 2005-272778 A | 10/2005 |
| JP | 2005-272785 A | 10/2005 |
| JP | 2006-1982 A | 1/2006 |
| JP | 2006-316127 A | 11/2006 |
| JP | 2007-90574 A | 4/2007 |
| JP | 2008-51851 A | 3/2008 |
| JP | 2009-263338 A | 11/2009 |
| JP | 2010-095672 A | 4/2010 |
| JP | 2010-190919 A | 9/2010 |
| JP | 2011-12141 A | 1/2011 |
| JP | 2011-102356 A | 5/2011 |
| JP | 2011-225863 A | 11/2011 |
| JP | 2012-167199 A | 9/2012 |
| JP | 2013-142073 A | 7/2013 |
| JP | 2013-209628 A | 10/2013 |
| JP | 2013-539450 A | 10/2013 |
| JP | 2013-541531 A | 11/2013 |
| KR | 10-2013-0072165 A | 7/2013 |
| WO | WO 2004/108787 A1 | 12/2004 |
| WO | 2012/112015 A2 | 8/2012 |
| WO | WO 2012/121291 A1 | 9/2012 |
| WO | WO 2013/095016 A1 | 6/2013 |
| WO | WO 2013/115212 A1 | 8/2013 |
| WO | WO 2013/157490 A1 | 10/2013 |

OTHER PUBLICATIONS

Bell et al: "Glycerin as a Renewable Feedstock for Epichlorohydrin Production. The GTE Process", Clean-Soil, Air, Water, Wiley—VCH Verlag GMBH & Co. KGAA, DE, vol. 36, No. 8, Aug. 1, 2008, pp. 657-661.

Extended Search Report issued by the European Patent Office in related European Patent Application No. 15761645.9 dated Sep. 25, 2017 (9 pages).

International Search Report (PCT/ISA/210) dated Jun. 16, 2015, by the Japanese Patent Office as the International Searching Authority for International Application No. PCT/JP2015/057165.

International Search Report (PCT/ISA/210) dated Apr. 28, 2015, by the Japanese Patent Office as the International Searching Authority for International Application No. PCT/JP2015/057166.

Extended Search Report issued by the European Patent Office in related European Patent Application No. 15760947.0-1302 dated Nov. 22, 2017 (8 pages).

Office Action issued by the Japanese Patent Office in related Japanese Patent Application No. 2016-507793 dated Jun. 5, 2018 (2 pages).

Office Action issued by the Chinese Patent Office in related Chinese Patent Application No. 201580011225.X dated Jun. 14, 2018 (17 pages).

PROCESS FOR PRODUCING EPISULFIDE COMPOUND FOR OPTICAL MATERIAL, EPISULFIDE-CONTAINING COMPOSITION, AND POLYMERIZABLE COMPOSITION FOR OPTICAL MATERIAL INCLUDING THE SAME COMPOSITION

TECHNICAL FIELD

The present invention relates to a process for producing an episulfide compound for an optical material, an episulfide-containing composition, and a polymerizable composition for an optical material including the same composition.

BACKGROUND ART

Compared with inorganic lenses, plastic lenses have a low weight, are not easily cracked, and can be dyed, and thus, recently, have rapidly become widespread in optical elements such as eyeglass lenses and camera lenses.

For resins for plastic lenses, there has been a demand for additional improvement in performance, and there has been a demand for an increase in the refractive index, an increase in the Abbe number, a decrease in the specific weight, an improvement of the heat resistance, and the like. Thus far, a variety of resin materials for lenses have been developed and put into use.

Among them, optical materials comprised of sulfide-based resins have a high refractive index and a high Abbe number and are being studied as ultrahigh refractive index materials having a refractive index of higher than 1.6. Sulfide-based resins are obtained by polymerizing a polymerizable composition including an episulfide compound (Patent Documents 1 to 4). In recent years, a variety of studies also have been carried out in order to improve the quality of episulfide compounds and resins for optical materials obtained from the episulfide compounds (Patent Documents 5 and 6).

Regarding epichlorohydrin as well which is a raw material of episulfide compounds, a producing route in which epichlorohydrin is synthesized by means of chlorination and epoxidation of glycerin originating from natural products has been developed instead of a producing route in which epichlorohydrin is synthesized from a fossil raw material (propylene, allyl alcohol, or the like) of the related art and the application of the producing route to epoxy resins and the like is being studied (Patent Document 7). However, no studies are being carried out regarding optical material use.

As plastic lens materials obtained using plant-derived materials, an eyeglass lens which includes a polycarbonate resin having a constituent unit derived from isosorbide as a main component and is obtained by means of injection molding is proposed (Patent Document 8). This enables the preparation of optical lenses having high heat resistance, high strength, and low distortion which are produced from plant-derived materials, but there is room for improvement in optical properties such as the refractive index.

Furthermore, in Patent Document 9, a resin comprised of plant-derived materials is proposed, but this resin is not for use as an ultrahigh refractive index material having a refractive index of higher than 1.6, and any optical properties and the like of the obtained resin are not exhibited.

RELATED DOCUMENT

Patent Document

[Patent Document 1] Japanese Unexamined Patent Publication No. 2002-194083

[Patent Document 2] Japanese Unexamined Patent Publication No. 2000-256435

[Patent Document 3] Japanese Unexamined Patent Publication No. 2001-163874

[Patent Document 4] Pamphlet of International Publication No. WO2013/115212

[Patent Document 5] Pamphlet of International Publication No. WO2013/157490

[Patent Document 6] Japanese Unexamined Patent Publication No. 2013-142073

[Patent Document 7] PCT Japanese Translation Patent Publication No. 2013-541531

[Patent Document 8] Japanese Unexamined Patent Publication No. 2010-190919

[Patent Document 9] Japanese Unexamined Patent Publication No. 2011-225863

SUMMARY OF THE INVENTION

An object of the present invention is to provide a process for producing an episulfide compound for an optical material that can be used to obtain an optical material which has an excellent balance among transparency, heat resistance, and the like and has an ultrahigh refractive index of higher than 1.60, an episulfide-containing composition obtained using the same producing method, and a composition for an optical material including the composition.

As a result of intensive studies, the present inventors found that, when an episulfide compound or an episulfide-containing composition which is obtained using a predetermined producing method is used, it is possible to provide optical materials such as ultrahigh refractive index plastic lenses having a refractive index of higher than 1.60 which have an excellent balance among transparency, refractive index, heat resistance, and the like and completed the present invention.

That is, the present invention can be described as below.

[1] A process for producing an episulfide compound for an optical material, comprising:

a step of chlorinating glycerin to obtain dichloropropanol;

a step of epoxidizing the dichloropropanol to obtain epichlorohydrin;

a step of reacting the epichlorohydrin with a sulfating agent to obtain a bis(chlorohydrin) (di)sulfide compound thought a thiol compound;

a step of epoxidizing the bis(chlorohydrin) (di)sulfide compound under basic conditions to obtain an epoxy compound; and a step of reacting the epoxy compound with a sulfating agent to obtain an episulfide compound represented by following General Formula (1):

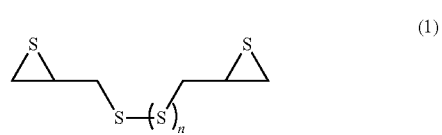

wherein, in the formula, n represents 0 or 1.

[2] The process for producing an episulfide compound for an optical material according to [1], wherein the glycerin is obtained from plant-derived materials.

[3] A process for producing an episulfide-containing composition, comprising:

a step of chlorinating glycerin in a composition a including the glycerin obtained from plant-derived materials to obtain a composition b including dichloropropanol;

a step of epoxidizing the dichloropropanol in the composition b to obtain a composition c including epichlorohydrin;

a step of reacting the epichlorohydrin with a sulfating agent in the composition c to obtain a composition d including a bis(chlorohydrin) (di)sulfide compound through a thiol compound;

a step of epoxidizing the bis(chlorohydrin) (di)sulfide compound under basic conditions in the composition d to obtain a composition e including an epoxy compound; and a step of reacting the epoxy compound with a sulfating agent in the composition e to obtain a composition f including an episulfide represented by following General Formula (1):

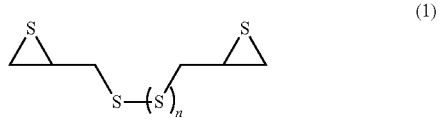

(1)

wherein, in the formula, n represents 0 or 1.

[4] An episulfide-containing composition represented by following General Formula (1) obtained using the producing method according to [3]:

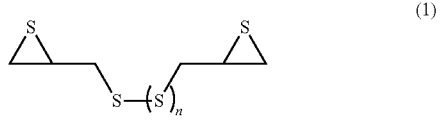

(1)

wherein, in the formula, n represents 0 or 1.

[5] A polymerizable composition for an optical material comprising:

the episulfide-containing composition according to [4].

[6] The polymerizable composition for an optical material according to [5], further comprising:

a polyisocyanate (a).

[7] The polymerizable composition for an optical material according to [6], wherein the polyisocyanate (a) is at least one selected from hexamethylene diisocyanate, isophorone diisocyanate, bis(isocyanatomethyl)cyclohexane, dicyclohexylmethane diisocyanate, 2,5-bis(isocyanatomethyl)bicyclo-[2.2.1]-heptane, 2,6-bis(isocyanatomethyl)bicyclo-[2.2.1]-heptane, m-xylylene diisocyanate, and 2,5-bis(isocyanatomethyl)-1,4-dithiane.

[8] The polymerizable composition for an optical material according to any one of [5] to [7], further comprising:

a polythiol (b).

[9] The polymerizable composition for an optical material according to [8], wherein the polythiol (b) is at least one selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis mercaptoacetate, pentaerythritol tetrakis mercaptopropionate, 2,5-bis(mercaptomethyl)-1,4-dithiane, bis(mercaptoethyl) sulfide, 1,1,3,3-tetrakis(mercaptomethylthio)propane, 4,6-bis(mercaptomethylthio)-1,3-dithiane, 2-(2,2-bis(mercaptomethylthio) ethyl)-1,3-dithietane, 1,1,2,2-tetrakis (mercaptomethylthio) ethane, 3-mercaptomethyl-1,5-dimercapto-2,4-dithiapentane, tris(mercaptomethylthio) methane, and ethylene glycol bis(3-mercaptopropionate).

[10] The polymerizable composition for an optical material according to [8] or [9], wherein the polythiol (b) is a polythiol obtained from plant-derived materials and is selected from 4-mercaptomethyl-1,8-dimercapto-3,6-dithiaoctane and 4,8 or 4,7 or 5,7-dimercaptomethyl-1,11-dimercapto-3,6,9-trithiaundecane.

[11] A molded product comprised of a resin obtained by polymerization-curing the polymerizable composition for an optical material according to any one of [5] to [10].

[12] The molded product according to [11], wherein a biomass ratio of the resin is 25% or higher.

[13] The molded product according to [11] or [12], wherein a glass transition temperature (Tg) is 60° C. or higher.

[14] An optical material comprised of the molded product according to any one of [11] to [13].

[15] A plastic eyeglass lens comprised of the molded product according to any one of [11] to [13].

[16] A plastic polarizing lens, wherein a layer comprised of the molded product according to any one of [11] to [13] is laminated over at least one surface of a polarizing film.

Meanwhile, in the present invention, "(di)sulfide compounds" refer to sulfide compounds or disulfide compounds.

When an episulfide compound or an episulfide-containing composition obtained using the producing method of the present invention is used, it is possible to obtain optical materials such as ultrahigh refractive index plastic lenses having a refractive index of higher than 1.60 which have an excellent balance among transparency, refractive index, heat resistance, and the like.

Furthermore, when an episulfide compound or an episulfide-containing composition obtained from plant-derived materials is used, it is possible to provide optical materials such as plastic lenses which have a biomass ratio of 25% or higher and, furthermore, is also excellent in terms of the above-described properties.

DESCRIPTION OF EMBODIMENTS

A process for producing an episulfide compound for an optical material of the present invention includes a step of chlorinating glycerin to obtain dichloropropanol;

a step of epoxidizing the dichloropropanol to obtain epichlorohydrin;

a step of reacting the epichlorohydrin with a sulfating agent to obtain a bis(chlorohydrin) (di)sulfide compound thought a thiol compound;

a step of epoxidizing the bis(chlorohydrin) (di)sulfide compound under basic conditions to obtain an epoxy compound; and a step of reacting the epoxy compound with a sulfating agent to obtain an episulfide compound represented by following General Formula (1).

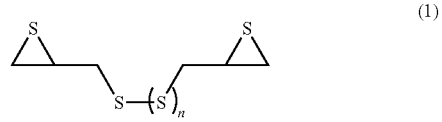

(1)

In the formula, n represents 0 or 1.

The episulfide compound represented by General Formula (1) is specifically bis(2,3-epithiopropyl) sulfide or bis(2,3-epithiopropyl) disulfide.

In the present embodiment, a process for producing the episulfide compound will be described.

(Process for Producing bis(2,3-epithiopropyl) sulfide)

In the present embodiment, a process for producing bis(2,3-epithiopropyl) sulfide which is an episulfide compound for an optical material includes the following steps as illustrated in following Reaction Formula (2).

(i) A step in which glycerin is chlorinated, thereby obtaining dichloropropanol (shown as a) in following Reaction Formula (2))

(ii) A step in which the dichloropropanol is epoxidized, thereby obtaining epichlorohydrin (shown as b) in following Reaction Formula (2))

(iii) A step in which the epichlorohydrin is reacted with a sulfating agent, thereby obtaining a thiol compound and then a bis(chlorohydrin) sulfide compound (shown as c) in following Reaction Formula (2))

(iv) A step in which the bis(chlorohydrin) sulfide compound is epoxidized under basic conditions, thereby obtaining an epoxy compound (shown as d) in following Reaction Formula (2))

(v) A step in which the epoxy compound is reacted with a sulfating agent, thereby obtaining bis(2,3-epithiopropyl) disulfide (shown as e) in following Reaction Formula (2))

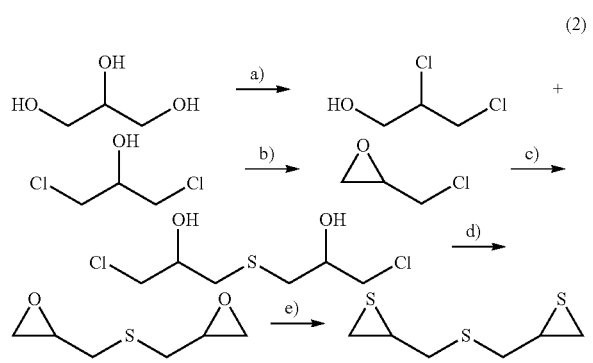

These steps will be described in detail below.

Step (i)

In a case in which glycerin is chlorinated, as a chlorinating agent, chlorine, hydrogen chloride, or the like can be used, and glycerin can be chlorinated in the presence or absence of a catalyst. Preferably, a reaction is performed in the presence of a preferred catalyst. In this case, a catalyst based on carboxylic acid or a carboxylic acid derivative, for example, a carboxylic acid anhydride, a carboxylic acid chloride, a carboxylate salt, or a carboxylic acid ester can be advantageously used.

Examples of the catalyst include at least one carboxylic acid selected from aliphatic acids such as acetic acid, formic acid, propionic acid, and butyric acid and aromatic carboxylic acid derivatives such as benzoic acid. The carboxylic acid may be a poly(carboxylic acid) such as di-, tri-, or tetracarboxylic acid, and among these, dicarboxylic acid is preferred.

In the chlorination reaction, as a solvent, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, or water is preferably used. These solvents may be used singly, or two or more solvents may be used in a mixture form.

The reaction temperature is preferably 20° C. to 160° C., more preferably 80° C. to 140° C., and still more preferably 90° C. to 120° C. In a case in which hydrogen chloride is used, this reaction is performed at a partial pressure of generally 0.002 bar or higher, preferably 0.02 bar or higher, and particularly preferably 0.05 bar or higher, and this pressure is generally 50 bar or lower, preferably 30 bar or lower, and particularly preferably 20 bar or lower.

Step (ii)

When epichlorohydrin is synthesized from dichloropropanol, the base equivalent is preferably in a range of 0.5 equivalents to 5 equivalents and more preferably in a range of 0.9 equivalents to 2.0 equivalents with respect to dichloropropanol. Examples of bases that can be used include organic or inorganic bases such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, and sodium acetate.

In a process for producing epichlorohydrin of the present invention, the reaction temperature is preferably 0° C. to 140° C. and more preferably 10° C. to 50° C. Examples of a solvent that can be used include aromatic solvents such as toluene, xylene, chlorobenzene, dichlorobenzene, and nitrobenzene, aliphatic solvents such as dichloromethane, chloroform, and dichloroethane, alcohols such as methanol, ethanol, isopropanol, butanol, methoxyethanol, ethylene glycol, and glycerin, and water. These solvents may be used singly, or two or more solvents may be used in a mixture form.

Step (iii)

A sulfating agent such as hydrogen sulfide, sodium hydrosulfide, or sodium sulfide is reacted with epichlorohydrin, thereby synthesizing 1-chloro-3-mercapto-2-propanol (a thiol compound) and then a bis(chlorohydrin) sulfide compound. In a case in which this thiol compound is synthesized first, it is also possible to directly obtain bischlorohydrin in the system without isolating the thiol compound. The used amount of the sulfating agent can be set in a range of 0.3 equivalents to 4 equivalents, preferably set in a range of 0.4 equivalents to 3 equivalents, and more preferably set in a range of 0.5 equivalents to 2 equivalents with respect to epichlorohydrin.

At this time, when an organic or inorganic base such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, or sodium acetate is added thereto as a reaction catalyst, there are many cases in which a preferred result is given. Among these bases, inorganic bases are relatively preferred, and, among inorganic bases, sodium hydroxide, potassium hydroxide, potassium carbonate, calcium hydroxide, and the like are preferred.

The added amount of the base is preferably in a range of 0.1 wt % to 10 wt % and more preferably in a range of 0.3 wt % to 5 wt % with respect to epichlorohydrin. The reaction temperature is preferably −20° C. to 50° C. and more preferably 0° C. to 40° C.

A reaction solvent may or may not be used, and, in a case in which a reaction solvent is used, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, water, or the like is preferably used.

These solvents may be used singly, or two or more solvents may be used in a mixture form.

In a case in which a two-phase separation-type mixed solvent system of, for example, water and an aromatic solvent or water and an aliphatic solvent is used, when a surfactant such as an alcohol, a quaternary alkyl ammonium salt, an alkyl or aryl carboxylic acid metal salt, an alkyl or aryl sulfonic acid metal salt, an acidic alkyl or an aryl phosphoric acid ester, or a metal salt thereof is added thereto as a phase-transfer catalyst, there are many cases in which a preferred result is given. The amount of the surfactant added is preferably in a range of 0.001 wt % to 20 wt % and more preferably in a range of 0.1 wt % to 10 wt % with respect to the total weight of a reaction mass.

Step (iv)

An organic or inorganic base such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, or sodium acetate is added to the reaction mass obtained in Step (iii), thereby obtaining a composition including an epoxy compound.

These bases may be used singly, or two or more bases may be jointly used. The kind of the base being used is relatively favorable inorganic base than an organic base, and, among inorganic bases, sodium hydroxide or potassium hydroxide is preferred. The used amount of the base is preferably in a range of 1 equivalent to 10 equivalents and more preferably in a range of 2 equivalents to 5 equivalents with respect to the previously-used epichlorohydrin. The reaction temperature is preferably −10° C. to 60° C. and more preferably 5° C. to 30° C. Generally, an epoxy compound represented by Reaction Formula (2) is synthesized using the above-described two-step method, but the epoxy compound can also be synthesized using a single-step method in which the equivalent or more of an organic or inorganic base with respect to epichlorohydrin is added thereto and then epichlorohydrin is added thereto. In Step (iv), a composition including the epoxy compound is obtained.

Step (v)

A composition including a thioepoxy compound (bis(2, 3-epithiopropyl) sulfide) can be obtained by reacting the epoxy compound with a sulfating agent in a composition including the epoxy compound obtained in Step (iv). Examples of the sulfating agent include thiocyanate salts such as thiourea, sodium thiocyanate, potassium thiocyanate, ammonium thiocyanate, calcium thiocyanate, and lead thiocyanate. In a case in which a thiocyanate salt is used, sodium thiocyanate, potassium thiocyanate, or ammonium thiocyanate is relatively preferred, and sodium thiocyanate is more preferred.

The used amount of thiourea or the thiocyanate salt, which is the sulfating agent, for example, the equivalent or more of the epoxy group, preferably in a range of 1 equivalent to 5 equivalents, and more preferably in a range of 1 equivalent to 3 equivalents. When an amount is less than 1 equivalent, these are cases in which the purity decreases, and, when the amount exceeds 5 equivalents, there are cases in which the method becomes economically disadvantageous.

The reaction temperature significantly varies depending on the kind of thiourea or the thiocyanate salt; however, in a case in which thiourea is used, the reaction temperature is preferably approximately 10° C. to 30° C., and in a case in which the thiocyanate salt is used, the reaction temperature is preferably 30° C. to 60° C.

In a case in which the thioepoxy compound is synthesized, generally, almost the same reaction solvent as that during the synthesis of the epoxy compound is used. For example, an aromatic solvent such as toluene, xylene, chlorobenzene, dichlorobenzene, or nitrobenzene, an aliphatic solvent such as dichloromethane, chloroform, or dichloroethane, or an alcohol such as methanol, ethanol, isopropanol, butanol, methoxyethanol, ethylene glycol, or glycerin is preferably used. These solvents may be used singly, or two or more solvents may be used in a mixture form. Unlike the case of epoxidization, in the case of thioepoxidization, there is a tendency of water decreasing the reaction rate, and thus water is not preferably used.

As in the producing method of the present embodiment, in epichlorohydrin produced from glycerin, the amount of impurities (chlorine-based byproducts and hydrolysable chlorine) is smaller than that in epichlorohydrin synthesized from a petroleum resource-derived raw material such as allyl chloride or propylene. Examples of the chlorine-based byproducts include allyl chloride, 1,2-dichloropropane, 2,3-dichloropropene, 2-chloroallyl alcohol, 1,3-dichloropropene, 1,2,3-trichloropropane, and the like. These chlorine-based byproducts are highly reactive and thus serve as a cause for generating byproducts in the producing of the episulfide compound. Therefore, when epichlorohydrin produced from glycerin is used, the quality such as color, storage stability, purification load, and the like of intermediate bodies or final products are excellent. These chlorine-based impurities have a boiling point close to that of epichlorohydrin and are not easily completely removed even by means of distillation.

The present inventors found that, for example, when dichloropropene, which is a chlorine-based byproduct, is reacted with chloromercaptopropanol, and thus chlorine-based impurities having a more complicated structure such as chloro-(2-chloroallyl)thio)propanol are generated, and furthermore, the content of impurities in the final product increases during the progress of the producing step, further found that, when epichlorohydrin produced from glycerin is used as a raw material, it is possible to suppress the generation of the above-described byproduct, and completed the present invention. Furthermore, the present inventors found that epichlorohydrin which is produced from glycerin obtained from plant-derived materials exhibits superior effects to the above-described effects and completed the present invention.

In epichlorohydrin obtained using the producing method of the present embodiment, the amount of the chlorine-based impurities is smaller than or equal to 5,000 ppm and preferably smaller than or equal to 4,500 ppm, smaller than or equal to 2,000 ppm, smaller than or equal to 150 ppm, or smaller than or equal to 50 ppm.

In the present embodiment, glycerin, epichlorohydrin, or the like including the above-described impurities can be referred to as a glycerin-containing composition, an epichlorohydrin-containing composition, or the like, respectively.

As a result, an episulfide compound having favorable quality such as color can be obtained, and thus there are advantages that the fluctuation in optical properties, the generation rate of optical strain, and the like in molded products are suppressed and the yield of optical products improves.

In the present embodiment, bis(2,3-epithiopropyl) sulfide, which is an episulfide compound, is synthesized using epichlorohydrin obtained by chlorinating glycerin and then epoxidizing obtained product as described above as a raw material. Glycerin which is used as a raw material may be derived from a fossil resource raw material or from a natural product, but glycerin originating from a natural product is preferred since it is possible to obtain an episulfide compound having a high biomass ratio. Glycerin is obtained by, for example, saponifying an oil and fat of a plant or an alga and the like.

In the present embodiment, bis(2,3-epithiopropyl) sulfide can be synthesized from glycerin obtained from plant-derived materials by using a composition including glycerin obtained from plant-derived materials as a reaction liquid form in the subsequent step as described below. Thereby, it is possible to obtain a bis(2,3-epithiopropyl) sulfide-containing composition (episulfide-containing composition).

(i) A step in which, in a composition including glycerin obtained from plant-derived materials, the glycerin is chlorinated, thereby obtaining a composition including dichloropanol (ii) A step in which, in the composition obtained in the (i), the dichloropropanol is epoxidized, thereby obtaining a composition including epichlorohydrin (iii) A step in which, in the composition obtained in the (ii), the epichlorohydrin is reacted with a sulfating agent, thereby obtaining a thiol compound and then a bis(chlorohydrin) sulfide compound (iv) A step in which, in the composition obtained in the (iii), the bis(chlorohydrin) sulfide compound is epoxidized under basic conditions, thereby obtaining a composition including an epoxy compound (v) A step in which, in the composition obtained in the (iv), the epoxy compound is reacted with a sulfating agent, thereby obtaining a composition including bis(2,3-epithiopropyl) sulfide The composition including glycerin obtained from plant-derived materials, which is used in Step (i), can be obtained from an aliphatic acid ester of glycerin included in a plant oil and fat such as canola oil, palm oil, castor oil, or olive oil or an oil and fat of an alga and the like by means of hydrolysis or ester-exchange.

Step (v) can include a step of purifying the composition.

When glycerin obtained from plant-derived materials is used as a raw material, it is possible to reduce the environmental load on the entire producing process of an optical material. Furthermore, the amount of impurities (chlorine-based byproducts and hydrolysable chlorine) in epichlorohydrin produced from glycerin is smaller than that in epichlorohydrin derived from a petroleum resource such as propylene. Therefore, in the producing of an episulfide compound, the quality such as color, storage stability, purification load, and the like of intermediates or final products are excellent.

As a result, when glycerin obtained from plant-derived materials is used as a raw material, contribution is made to the preservation of the global environment, and episulfide compounds having favorable quality can be obtained, and thus there are advantages that the fluctuation in optical properties, the generation rate of optical strain, and the like are suppressed and, also, the yield of optical products improves.

(Process for Producing bis(2,3-epithiopropyl) disulfide)

A method for synthesizing bis(2,3-epithiopropyl) disulfide which is an episulfide compound for an optical material includes the following steps as illustrated in Reaction Formula (3) below.

(i) A step in which glycerin is chlorinated, thereby obtaining dichloropropanol (a) in Reaction Formula (3) below (ii) A step in which the dichloropropanol is epoxidized, thereby obtaining epichlorohydrin (b) in Reaction Formula (3) below (iii) A step in which the epichlorohydrin is reacted with a sulfating agent, thereby obtaining bischlorohydrin and then the bischlorohydrin is oxidized, thereby obtaining a bis (chlorohydrin) sulfide compound (c) in Reaction Formula (3) below (iv) A step in which the bis(chlorohydrin) sulfide compound is epoxidized under basic conditions, thereby obtaining an epoxy compound (d) in Reaction Formula (3) below (v) A step in which the epoxy compound is reacted with a sulfating agent, thereby obtaining bis(2,3-epithiopropyl) disulfide (e) in Reaction Formula (3) below

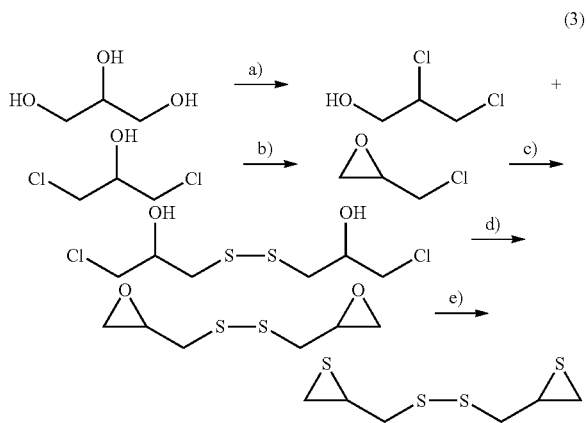

These steps will be described in detail below.

Step (i)

In a case in which glycerin is chlorinated, as a chlorinating agent, chlorine, hydrogen chloride, or the like can be used, and glycerin can be chlorinated in the presence or absence of a catalyst. Preferably, a reaction is performed in the presence of a preferred catalyst. In this case, a catalyst based on carboxylic acid or a carboxylic acid derivative, for example, a carboxylic acid anhydride, a carboxylic acid chloride, a carboxylate salt, or a carboxylic acid ester can be advantageously used.

Examples of the catalyst include at least one carboxylic acid selected from aliphatic acids such as acetic acid, formic acid, propionic acid, and butyric acid and aromatic carboxylic acid derivatives such as benzoic acid. The carboxylic acid may be a poly(carboxylic acid) such as di-, tri-, or tetracarboxylic acid, and among these, dicarboxylic acid is preferred.

As a reaction solvent, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin is preferably used. These solvents may be used singly, or two or more solvents may be used in a mixture form.

The reaction temperature is preferably 20° C. to 160° C., more preferably 80° C. to 140° C., and still more preferably 90° C. to 120° C. In a case in which hydrogen chloride is used, this reaction is performed at a partial pressure of hydrogen chloride of generally 0.002 bar or higher, preferably 0.02 bar or higher, and particularly preferably 0.05 bar or higher, and this pressure is generally 50 bar or lower, preferably 30 bar or lower, and particularly preferably 20 bar or lower.

Step (ii)

When epichlorohydrin is synthesized from dichloropropanol, the base is preferably in a range of 0.5 equivalents to 5 equivalents and more preferably in a range of 0.9 equivalents to 2.0 equivalents with respect to dichloropropanol. Examples of bases that can be used include organic or inorganic bases such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, and sodium acetate.

In a process for producing epichlorohydrin, the reaction temperature is preferably 0° C. to 140° C. and more preferably 10° C. to 50° C. Examples of a solvent that can be used include aromatic solvents such as toluene, xylene, chlorobenzene, dichlorobenzene, and nitrobenzene, aliphatic solvents such as dichloromethane, chloroform, and dichloroethane, alcohols such as methanol, ethanol, isopropanol, butanol, methoxyethanol, ethylene glycol, and glycerin. These solvents may be used singly, or two or more solvents may be used in a mixture form.

Step (iii)

A sulfating agent such as hydrogen sulfide, sodium hydrosulfide, or sodium sulfide is reacted with epichlorohydrin, thereby synthesizing 1-chloro-3-mercapto-2-propanol (a thiol compound) and then a bis(chlorohydrin) disulfide compound. The used amount of the sulfating agent is preferably in a range of 0.5 equivalents to 2 equivalents and more preferably in a range of 0.9 equivalents to 1.2 equivalents with respect to epichlorohydrin.

At this time, when an organic or inorganic base such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, or sodium acetate is added thereto as a reaction catalyst, there are many cases in which a preferred result is given. Among these bases, inorganic bases are relatively preferred, and, among inorganic bases, sodium hydroxide, potassium hydroxide, potassium carbonate, calcium hydroxide, and the like are preferred. The amount of the base added is preferably in a range of 0.1 wt % to 10 wt % and more preferably in a range of 0.3 wt % to 5 wt % with respect to epichlorohydrin. The reaction temperature is preferably −20° C. to 50° C. and more preferably 0° C. to 30° C.

A reaction solvent may or may not be used, and, in a case in which a reaction solvent is used, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, water, or the like is preferably used. These solvents may be used singly, or two or more solvents may be used in a mixture form. In a case in which a two-phase separation-type mixed solvent system of, for example, water and an aromatic solvent or water and an aliphatic solvent is used, in a case in which a surfactant such as an alcohol, a quaternary alkyl ammonium salt, an alkyl or aryl carboxylic acid metal salt, an alkyl or aryl sulfonic acid metal salt, an acidic alkyl or an aryl phosphoric acid ester, or a metal salt thereof is added thereto as a phase-transfer catalyst, there are many cases in which a preferred result is given. The amount of the surfactant added is preferably in a range of 0.001 wt % to 20 wt % and more preferably in a range of 0.1 wt % to 10 wt % with respect to the total weight of a reaction mass.

1-Chloro-3-mercapto-2-propanol which is the obtained thiol compound is made into a disulfide using an oxidant such as chlorine, bromine, iodine, hydrogen peroxide, or sodium hypochlorite, whereby a bis(chlorohydrin) disulfide compound can be obtained. The used amount of the oxidant is preferably in a range of 0.2 equivalents to 5 equivalents and more preferably in a range of 0.4 equivalents to 2.0 equivalents with respect to epichlorohydrin. The reaction temperature is preferably 0° C. to 50° C. and more preferably 0° C. to 30° C. A reaction solvent may or may not be used, and, in a case in which a reaction solvent is used, an aromatic solvent such as toluene, xylene, chlorobenzene, dichlorobenzene, or nitrobenzene, an aliphatic solvent such as dichloromethane, chloroform, or dichloroethane, an alcohol such as methanol, ethanol, isopropanol, butanol, methoxyethanol, ethylene glycol, or glycerin, water, or the like is preferably used.

Step (iv)

An organic or inorganic base such as triethylamine, tributylamine, dimethylcyclohexylamine, diethylaniline, pyridine, sodium hydroxide, potassium hydroxide, magnesium hydroxide, calcium hydroxide, sodium carbonate, sodium hydrogen carbonate, potassium carbonate, sodium methylate, t-butoxy potassium, disodium monohydrogen phosphate, or sodium acetate is added to the reaction mass obtained in Step (iii), thereby obtaining a composition including an epoxy compound.

These bases may be used singly, or two or more bases may be jointly used. The kind of the base being used is more preferably an inorganic base than an organic base, and, among inorganic bases, sodium hydroxide or potassium hydroxide is preferred. The used amount of the base is preferably in a range of 1 equivalent to 10 equivalents and more preferably in a range of 2 equivalents to 5 equivalents with respect to the previously-used epichlorohydrin.

In addition, the reaction temperature is preferably −10° C. to 60° C. and more preferably 5° C. to 30° C. Generally, the epoxy compound according to the present invention is synthesized using the above-described two-step method, but the epoxy compound can also be synthesized using a single-step method in which the equivalent or more of an organic or inorganic base with respect to epichlorohydrin is added thereto and then epichlorohydrin is added thereto. In Step (iv), a composition including the epoxy compound is obtained.

Step (v)

A composition including a thioepoxy compound (bis(2,3-epithiopropyl) disulfide) can be obtained by reacting the epoxy compound with a sulfating agent in a composition including the epoxy compound obtained in Step (iv). Examples of the sulfating agent include thiourea, thiocyanate salts such as sodium thiocyanate, potassium thiocyanate, ammonium thiocyanate, calcium thiocyanate, and lead thiocyanate. In a case in which a thiocyanate salt is used, sodium thiocyanate, potassium thiocyanate, or ammonium thiocyanate is preferred, and sodium thiocyanate is more preferred.

The used amount of thiourea or the thiocyanate salt, which is the sulfating agent, for example, the equivalent or more of the epoxy group, preferably in a range of 1 equivalent to 5 equivalents, and more preferably in a range of 1 equivalent to 3 equivalents. At an amount of less than 1 equivalent, the purity decreases, and, when the amount exceeds 5 equivalents, there are cases in which the method becomes economically disadvantageous.

The reaction temperature significantly varies depending on the kind of thiourea or the thiocyanate salt and is thus not particularly limited; however, in a case in which thiourea is used, the reaction temperature is preferably approximately 10° C. to 30° C., and in a case in which the thiocyanate salt is used, the reaction temperature is preferably 30° C. to 60° C.

In a case in which the thioepoxy compound is synthesized, generally, almost the same reaction solvent as that during the synthesis of the epoxy compound is used. For example, an aromatic solvent such as toluene, xylene, chlorobenzene, dichlorobenzene, or nitrobenzene, an aliphatic solvent such as dichloromethane, chloroform, or dichloroethane, or an alcohol such as methanol, ethanol, isopropanol, butanol, methoxyethanol, ethylene glycol, or glycerin is preferably used. These solvents may be used singly, or two or more solvents may be used in a mixture form. Unlike the case of epoxidization, in the case of thioepoxidization, there is a tendency of water decreasing the reaction rate, and thus water is not preferably used.

The amount of impurities (chlorine-based byproducts and hydrolysable chlorine) in epichlorohydrin produced from glycerin is smaller than that in epichlorohydrin derived from a petroleum resource such as propylene. Therefore, in the producing of an episulfide compound, the quality such as color, storage stability, purification load, and the like of intermediate bodies or final products are excellent.

As a result, episulfide compounds having favorable quality can be obtained, and thus there are advantages that the fluctuation in optical properties, the generation rate of optical strain, and the like are suppressed and, also, the yield of optical products improves.

In the present embodiment, bis(2,3-epithiopropyl) disulfide, which is an episulfide compound, is synthesized using epichlorohydrin obtained by chlorinating glycerin and epoxidizing an obtained product as described above as a raw material. Glycerin which is used as a raw material may be derived from a fossil resource raw material or from a natural product, but glycerin originating from a natural product is preferred since it is possible to obtain an episulfide compound having a high biomass ratio. Glycerin is obtained by, for example, saponifying an oil and fat of a plant, an alga and the like.

In the present embodiment, bis(2,3-epithopropyl) disulfide can be synthesized from glycerin obtained from plant-derived materials by using a composition including glycerin obtained from plant-derived materials as described below in a reaction liquid form in the subsequent step. Therefore, it is possible to obtain a bis(2,3-epithiopropyl) disulfide-containing composition (episulfide-containing composition).

Meanwhile, the reaction conditions are identical to those of Steps (i) to (v).

(i) A step in which, in a composition a including glycerin obtained from plant-derived materials, the glycerin is chlorinated, thereby obtaining a composition including dichloropropanol (ii) A step in which, in the composition obtained in the (i), the dichloropropanol is epoxidized, thereby obtaining a composition including epichlorohydrin (iii) A step in which, in the composition obtained in the (ii), the epichlorohydrin is reacted with a sulfating agent and then is oxidized, thereby obtaining composition including a bis(chlorohydrin) disulfide compound (iv) A step in which, in the composition obtained in the (iii), the bis(chlorohydrin) disulfide compound is epoxidized under basic conditions, thereby obtaining a composition including an epoxy compound (v) A step in which, in the composition obtained in the (iv), the epoxy compound is reacted with a sulfating agent, thereby obtaining a composition including bis(2,3-epithiopropyl) disulfide The composition including glycerin obtained from plant-derived materials, which is used in Step (i), can be obtained from an aliphatic acid ester of glycerin included in a plant oil and fat such as canola oil, palm oil, castor oil, or olive oil or an oil and fat of an alga and the like by means of hydrolysis or ester-exchange.

Step (v) can include a step of purifying the composition.

When glycerin obtained from plant-derived materials is used as a raw material, it is possible to reduce the environmental load on the entire producing process of an optical material. Furthermore, the amount of impurities (chlorine-based byproducts and hydrolysable chlorine) in epichlorohydrin produced from glycerin is smaller than that in epichlorohydrin derived from a petroleum resource such as propylene. Therefore, in the producing of an episulfide compound, the quality such as color, storage stability, purification load, and the like of intermediate bodies or final products are excellent.

As a result, when glycerin obtained from plant-derived materials is used as a raw material, contribution is made to the preservation of the global environment, and episulfide compounds having favorable quality can be obtained, and thus there are advantages that the fluctuation in optical properties, the generation rate of optical strain, and the like are suppressed and, also, the yield of optical products improves.

[Polymerizable composition for optical material] A polymerizable composition for an optical material of the present embodiment includes the above-described episulfide compound or episulfide-containing composition and is capable of further including a polyisocyanate (a) and a polythiol (b).

First, the respective components will be described.

(Polyisocyanate (a))

Examples of the polyisocyanate (a) include aliphatic polyisocyanate compounds such as hexamethylene diisocyanate, 2,2,4-trimethylhexane diisocyanate, 2,4,4-trimethylhexamethylene diisocyanate, lysine diisocyanatomethyl ester, lysine triisocyanate, m-xylylene diisocyanate, α,α,α',α'-tetramethylxylylene diisocyanate, bis(isocyanatomethyl) naphthalene, mesitylylene triisocyanate, bis(isocyanatomethyl) sulfide, bis(isocyanatoethyl) sulfide, bis(isocyanatomethyl) disulfide, bis(isocyanatoethyl) disulfide, bis(isocyanatomethylthio) methane, bis(isocyanatoethylthio) methane, bis(isocyanatoethylthio) ethane, and bis(isocyanatomethylthio) ethane;

alicyclic polyisocyanate compounds such as isophorone diisocyanate, bis(isocyanatomethyl) cyclohexane, dicyclohexylmethane diisocyanate, cyclohexane diisocyanate, methylcyclohexane diisocyanate, dicyclohexyldimethylmethane isocyanate, 2,5-bis(isocyanatomethyl)bicycle-[2.2.1]-heptane, 2,6-bis(isocyanatomethyl)bicyclo-[2.2.1]-heptane, 3,8-bis(isocyanatomethyl) tricyclodecane, 3,9-bis(isocyanatomethyl) tricyclodecane, 4,8-bis(isocyanatomethyl) tricyclodecane, and 4,9-bis(isocyanatomethyl) tricyclodecane;

aromatic polyisocyanate compounds such as phenylene diisocyanate, tolylene diisocyanate, 4,4-diphenylmethane diisocyanate, diphenylsulfide-4,4-diisocyanate; heterocyclic polyisocyanate compounds such as 2,5-diisocyanate thiophene, 2,5-bis(isocyanatomethyl) thiophene, 2,5-diisocyanate tetrahydrothiophene, 2,5-bis(isocyanatomethyl) tetrahydrothiophene, 3,4-bis(isocyanatomethyl) tetrahydrothiophene, 2,5-diisocyanate-1,4-dithiane, 2,5-bis(isocyanatomethyl)-1,4-dithiane, 4,5-diisocyanato-1,3-dithiolane, and 4,5-bis(isocyanatomethyl)-1,3-dithiolane, and the polyisocyanate can be used singly or two or more polyisocyanates can be jointly used.

Furthermore, it is also possible to use a halogen-substituted product such as a chlorine-substituted product or a bromine-substituted product, an alkyl-substituted product, an alkoxy-substituted product, or a nitro-substituted product of the isocyanate compound, a prepolymer derivative substance with a polyvalent alcohol, a carbodiimide derivative substance, an urea derivative substance, a biuret derivative substance, a dimerization or trimerization reaction product, or the like. These isocyanate compounds can be used singly, or two or more isocyanate compounds can also be used in a mixture form.

Among these polyisocyanate compounds, from the viewpoint of ease of procurement, price, the performance of the obtained resin, and the like, diisocyanate compounds are preferably used. For example, the polyisocyanate compound is preferably at least one selected from hexamethylene diisocyanate, isophorone diisocyanate, bis(isocyanatomethyl)cyclohexane, dicyclohexylmethane diisocyanate, 2,5-bis(isocyanatomethyl)bicyclo-[2.2.1]-heptane, 2,6-bis(isocyanatomethyl)bicyclo-[2.2.1]-heptane, m-xylylene diisocyanate, and 2,5-bis(isocyanatomethyl)-1,4-dithian, and particularly preferably at least one selected from 2,5-bis(isocyanatomethyl)bicyclo-[2.2.1]-heptane, 2,6-bis(isocyanatomethyl)bicyclo-[2.2.1]-heptane, and m-xylylene diisocyanate.

[Polythiol (b)]

In the present embodiment, examples of the polythiol compound (b) include aliphatic polythiol compounds such as methanedithiol, 1,2-ethanedithiol, 1,2,3-propanetrithiol, 1,2-cyclohexanedithiol, bis(2-mercaptoethyl) ether, tetrakis(mercaptomethyl) methane, diethylene glycol bis(2-mercaptoacetate), diethylene glycol bis(3-mercaptopropionate), ethylene glycol bis(2-mercaptoacetate), ethylene glycol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptomethylthio) methane, bis(2-mercaptoethylthio) methane, bis(3-mercaptopropylthio) methane, 1,2-bis(mercaptomethylthio) ethane, 1,2-bis(2-mercaptoethylthio) ethane, 1,2-bis(3-mercaptopropylthio) ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl) methane, tetrakis(2-mercaptoethylthiomethyl) methane, tetrakis(3-mercaptopropylthiomethyl) methane, bis(2,3-dimercaptopropyl) sulfide, 2,5-dimercaptomethyl-1,4-dithiane, 2,5-dimercapto-1,4-dithiane, 2,5-dimercaptomethyl-2,5-dimethyl-1,4-dithiane, esters of thioglycolic acids and mercaptopropionic acids thereof, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), bis(2-mercaptoethyl ester) thiodiglycolate, bis(2-mercaptoethyl ester) thiodipropionate, bis(2-mercaptoethyl ester) dithiodiglycolate, bis(2-mercaptoethyl ester) dithiodipropionate, 1,1,3,3-tetrakis(mercaptomethylthio)propane, 1,1,2,2-tetrakis(mercaptomethylthio) ethane, 4,6-bis(mercaptomethylthio)-1,3-dithiacyclohexane, tris(mercaptomethylthio) methane, and tris(mercaptoethylthio) methane;

aromatic polythiol compounds such as 1,2-dimercapto benzene, 1,3-dimercapto benzene, 1,4-dimercapto benzene, 1,2-bis(mercaptomethyl) benzene, 1,3-bis(mercaptomethyl) benzene, 1,4-bis(mercaptomethyl) benzene, 1,2-bis(mercaptoethyl) benzene, 1,3-bis(mercaptoethyl) benzene, 1,4-bis(mercaptoethyl) benzene, 1,3,5-trimercapto benzene, 1,3,5-tris(mercaptomethyl) benzene, 1,3,5-tris(mercaptomethyleneoxy) benzene, 1,3,5-tris(mercaptoethyleneoxy) benzene, 2,5-toluene dithiol, 3,4-toluene dithiol, 1,5-naphthalene dithiol, and 2,6-naphthalene dithiol;

heterocyclic polythiol compounds such as 2-methylamino-4,6-dithiol-sym-triazine, 3,4-thiophene dithiol, bismuthiol, 4,6-bis(mercaptomethylthio)-1,3-dithiane, and 2-(2,2-bis(mercaptomethylthio) ethyl)-1,3-dithietane, and these polythiol compounds can be used singly, or two or more polythiol compounds can be used in combination.

The polythiol (b) is preferably one selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis mercaptoacetate, pentaerythritol tetrakis(2-mercaptoacetate), pentaerythritol tetrakis mercaptopropionate, pentaerythritol tetrakis(3-mercaptopropionate), 2,5-bis(mercaptomethyl)-1,4-dithiane, bis(mercaptoethyl) sulfide, 1,1,3,3-tetrakis(mercaptomethylthio)propane, 4,6-bis(mercaptomethylthio)-1,3-dithiane, 2-(2,2-bis(mercaptomethylthio) ethyl)-1,3-dithietane, 1,1,2,2-tetrakis(mercaptomethyl) ethane, 3-mercaptomethyl-1,5-dimercapto-2,4-dithiapentane, tris(mercaptomethylthio) methane, and ethylene glycol bis(3-mercaptopropionate).

The polythiol (b) is more preferably selected from 4-mercaptomethyl-1,8-dimercapto-3,6-dithiaoctane and 4,8 or 4,7 or 5,7-dimercaptomethyl-1,11-dimercapto-3,6,9-trithiaundecane which are polythiols obtained from plant-derived materials.

(Polymerization Catalyst)

When the polymerizable composition of the present embodiment is heated or left to stand at room temperature in the presence or absence of a polymerization catalyst so as to be polymerized, it is possible to manufacture resins.

As the kinds of the present polymerization catalyst, amines, phosphines, organic acids and salts thereof, esters, anhydrides, inorganic acids, quaternary ammonium salts, quaternary phosphonium salts, tertiary sulfonium salts, secondary iodonium salts, Lewis acids, radical polymerization catalysts, cationic polymerization catalysts, and the like are generally used.

The polymerization catalyst may be used singly, or two or more polymerization catalysts may be used in a mixture form, and, when two or more polymerization catalysts having different reactive properties are jointly used out of the above-described polymerization catalysts, there are cases in which the handling properties of monomers and the optical properties, color, transparency, and optical strain (striae) of resins being obtained improve, and thus there are preferable cases.

Regarding specific examples of preferred curing catalysts, examples of amines include tertiary amines such as triethylamine, tri-n-propylamine, triisopropylamine, tri-n-butylamine, triisobutylamine, N,N-dimethylbenzylamine, N-methylmorpholine, N,N-dimethylcyclohexylamine, dimethyldipropylenetriamine, pentamethyldiethylenetriamine, bis(2-dimethylaminoethyl) ether, N-methylmorpholine, N,N'-dimethylpiperazine, triethylenediamine, N,N,N',N'-tetramethylethylenediamine, and bicyclooctanediamine (DABCO), quaternary ammonium salts such as tetramethylammonium bromide, tetraethylammonium bromide, tetrapropylammonium bromide, tetrabutylammonium bromide, tetrahexylammonium bromide, and tetraethyl ammonium hydroxide, for example, imidazoles such as imidazole, 1,2-dimethyl imidazole, benzyl methyl imidazole, and 2-ethyl-4-imidazole, for example, pyrazoles such as pyrazole, 3,5-dimethylpyrazole, for example, hindered amines such as 1,2,2,6,6-pentamethyl-4-piperidinol, 1,2,2,6,6-pentamethyl-4-hydroxyethyl-4-piperidinol, methyl-1,2,2,6,6-pentamethyl-4-piperidyl sebacate, mixtures of methyl-1,2,2,6,6-pentamethyl-4-piperidyl sebacate and bis(1,2,2,6,6-pentamethyl-4-piperidyl) sebacate, bis(1,2,2,6,6-pentamethyl-4-piperidyl) sebacate, bis(2,2,6,6-tetramethyl-1-(octyloxy)-4-piperidyl) sebacate, bis(1,2,2,6,6-pentamethyl-4-piperidyl) [[3,5-bis(1,1-dimethylethyl)-4-hydroxyphenyl]methyl] butylmalonate, and tetrakis(1,2,2,6,6-pentamethyl-4-piperidyl) butane-1,2,3,4-tetracarboxylate. Additionally, examples thereof include phosphines such as trimethylphosphine, triethylphosphine, tri-n-propylphosphine, triisopropylphosphine, tri-n-butylphosphine, triphenylphosphine, tribenzylphosphine, 1,2-bis(diphenylphosphino) ethane, and 1,2-bis(dimethylphosphino) ethane, Lewis acids such as dimethyl tin dichloride, dibutyl tin dichloride, dibutyl tin dilaurate, tetrachloro tin, dibutyl tin oxide, zinc chloride, zinc acetylacetone, aluminum chloride, aluminum fluoride, triphenyl aluminum, tetrachlorotitanium, and calcium acetate, and cationic polymerization catalysts such as diphenyliodonium hexafluorophosphate, diphenyliodonium hexafluoroarsenate, diphenyliodonium hexafluoroantimonate, triphenylsulfonium tetrafluoroborate, triphenylsulfonium hexafluorophosphate, and triphenylsulfonium hexafluoroarsenate, but the curing catalyst is not limited to these exemplary compounds.

The curing catalyst may be used singly, or two or more curing catalysts may be jointly used.

The amount of the curing catalyst added is in a range of 0.001 wt % to 10 wt % and preferably in a range of 0.01 wt % to 1 wt % with respect to the total weight of the composition including the episulfide compound represented by Formula (1).

(Sulfur)

To the polymerizable composition of the present embodiment, it is possible to add sulfur in order to improve the refractive index of molded products to be obtained. For sulfur that is used for optical resins, the purity thereof is preferably 98% or higher, more preferably 99% or higher, and still more preferably 99.5% or higher. In order to increase the purity, there are cases in which a method for removing a volatile component is also preferred.

Regarding the properties, sulfur may have any forms as long as the sulfur can be dissolved in the polymerizable composition, but a powder form is preferred, and a fine powder form is more preferred.

In a case in which the total weight of the episulfide compound and sulfur is set to 100 parts by weight, the amount of sulfur added is in a range of 10 parts by weight to 50 parts by weight, preferably in a range of 10 parts by weight to 40 parts by weight, and more preferably in a range of 10 parts by weight to 30 parts by weight. During addition, a well-known vulcanization catalyst such as an imidazole or an amine can be jointly used.

(Resin Modifier)

Examples of a resin modifier include epoxy compounds, olefins including (meth)acrylates, amino compounds, thiol compounds, polyphenols, amino acid and mercaptoamines, organic acids, anhydrides, and mercapto organic acids.

(Other Additives)

In addition to the resin modifier, a variety of well-known additives such as an internal mold release agent, a light stabilizer, a bluing agent, an ultraviolet absorber, an antioxidant, a dye, and a filler may be added thereto depending on the purpose as long as no problems are caused. As the internal mold release agent, an acidic phosphoric acid ester represented by following General Formula (4) can be used.

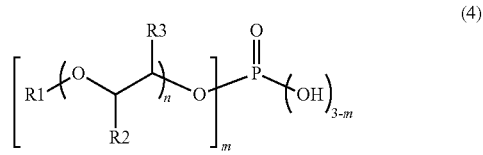

(4)

In the formula, m represents an integer of 1 or 2, n represents an integer of 0 to 18, R1 represents an alkyl group having 1 to 20 carbon atoms, and each of R2 and R3 independently represents a hydrogen atom, a methyl group, or an ethyl group. The number of carbon atoms in [ ]$_m$ is preferably 4 to 20.

Examples of R1 in General Formula (4) include organic residues derived from a linear aliphatic compound such as methane, ethane, propane, butane, pentane, hexane, heptane, octane, nonane, decane, undecane, dodecane, tetradecane, and hexadecane;

organic residues derived from a branched aliphatic compound such as 2-methylpropane, 2-methylbutane, 2-methylpentane, 3-methylpentane, 3-ethylpentane, 2-methylhexane, 3-methylhexane, 3-ethylhexane, 2-methylheptane, 3-methylheptane 4-methylheptane, 3-ethylheptane, 4-ethylheptane, 4-propylheptane, 2-methyloctane, 3-methyloctane, 4-methyloctane, 3-ethyloctane, 4-ethyloctane, and 4-propyloctane;

organic residues derived from alicyclic compounds such as cyclopentane, cyclohexane, 1,2-dimethylcyclohexane, 1,3-dimethylcyclohexane, and 1,4-dimethylcyclohexane; and the like, but R1 is not limited to these exemplary compounds.

Examples of commercially available products of the acidic phosphoric acid ester include Zelec UN manufactured by Stepan Company, JP series manufactured by Johoku Chemical Co., Ltd., PHOSPHANOL series manufactured by Toho Chemical Industry Co., Ltd., AP and DP series manufactured by Daihachi Chemical Industry Co., Ltd., and the like.

As the light stabilizer, hindered amine-based compounds can be used.

Examples of the hindered amine-based compounds include Lowilite 76 and Lowilite 92 manufactured by Chemtura Corporation, Tinuvin 123, Tinuvin 144, Tinuvin 292, Tinuvin 765, and Tinuvin 770DF manufactured by BASF, Adekastab LA-52 and LA-72 manufactured by ADEKA Corporation, JF-90 and JF-95 manufactured by Johoku Chemical Co., Ltd., and the like.

Examples of the bluing agent include bluing agents which have an absorption band in a wavelength range from orange color to yellow color in the visible light range and have a function of adjusting the colors of optical materials comprised of a resin. More specific examples of the bluing agent include substances exhibiting blue color through violet color.

Examples of the ultraviolet absorber include benzophenone-based ultraviolet absorbers such as 2,2'-dihydroxy-4-methoxybenzophenone, 2-hydroxy-4-acryloyloxy benzophenone, 2-hydroxy-4-acryloyloxy-5-tert-butyl benzophenone, and 2-hydroxy-4-acryloyloxy-2',4'-dichlorobenzophenone, triazine-based ultraviolet absorbers such as 2-[4-[(2-hydroxy-3-dodecyloxypropyl)oxy]-2-hydroxyphenyl]4,6-bis(2,4-dimethylphenyl)-1,3,5-triazine, 2-[4-(2-hydroxy-3-tridecyloxypropyl)oxy]-2-hydroxyphenyl]-4,6-bis(2,4-dimethylphenyl)-1,3,5-triazine, 2-[4-[(2-hydroxy-3-(2'-ethyl)hexyl)oxy]-2-hydroxyphenyl]-4,6-bis (2,4-dimethylphenyl)-1,3,5-triazine, 2,4-bis(2-hydroxy-4-butyloxyphenyl)-6-(2,4-bis-butyloxyphenyl)-1,3,5-triazine, and 2-(2-hydroxy-4-[1-octyloxycarbonylethoxy] phenyl)-4,6-bis(4-phenylphenyl)-1,3,5-triazine; and benzotriazole-based ultraviolet absorbers such as 2-(2H-benzotriazol-2-yl)-4-methylphenol, 2-(2H-benzotriazol-2-yl)-4-tert-octylphenol, 2-(2H-benzotriazol-2-yl)-4,6-bis(1-methyl-1-phenylethyl) phenol, 2-(2H-benzotriazol-2-yl)-4,6-di-tert-pentylphenol, 2-(5-chloro-2H-benzotriazol-2-yl)-4-methyl-6-tert-butylphenol, 2-(5-chloro-2H-benzotriazol-2-yl)-2,4-tert-butylphenol, and 2,2'-methylenebis[6-(2H-benzotriazol-2-yl)-4-(1,1,3,3-tetramethylbutyl) phenol]; and the like, and preferred examples thereof include benzotriazole-based ultraviolet absorbers such as 2-(2H-benzotriazol-2-yl)-4-tert-octylphenol and 2-(5-chloro-2H-benzotriazol-2-yl)-4-methyl-6-tert-butylphenol. These ultraviolet absorbers can be used singly or two or more ultraviolet absorbers can be jointly used.

The amount of these additives added is preferably in a range of 0.05 parts by weight to 2.0 parts by weight and more preferably in a range of 0.05 parts by weight to 1.5 parts by weight with respect to a total of 100 parts by mass of the constituent components.

The polymerizable composition for an optical material of the present embodiment can be obtained by mixing the above-described components. Regarding a mixing method, the components can be mixed using a well-known method of the related art.

The polymerizable composition of the present embodiment is a polymerizable composition a) including the above-described episulfide-containing composition, a polymerizable composition b) further including a polythiol compound in the above-described episulfide-containing composition, or a polymerizable composition c) further including a polythiol compound and a polyisocyanate compound in the above-described episulfide-containing composition.

From the viewpoint of having a high biomass ratio, the polymerizable composition preferably includes a monomer component produced from a plant-derived material, and the episulfide-containing composition in the polymerizable composition a) is produced from a plant-derived material. In the polymerizable composition b), at least one of the episulfide-containing composition and the polythiol compound is produced from a plant-derived material. In the polymerizable composition c), at least one of the episulfide-containing composition, the polythiol compound, and the polyisocyanate composition is produced from a plant-derived material.

The polymerizable composition for an optical material of the present embodiment can be obtained by mixing the above-described components. Regarding a mixing method, the components can be mixed using a well-known method of the related art.

In the polymerizable composition for an optical material of the present embodiment, the molar ratio of all mercapto groups in the polythiol (b) is in a range of 0.8 to 1.2, preferably in a range of 0.85 to 1.15, and more preferably in a range of 0.9 to 1.1 with respect to all isocyanate groups in the polyisocyanate (a). In the above-described range, it is possible to obtain a polymerizable composition for an optical material that is preferably used as an optical material, particularly, an eyeglass lens.

[Molded Product]

When the polymerizable composition for an optical material of the present embodiment is polymerization-cured, it is possible to obtain molded products having excellent properties such as transparency, refractive index, heat resistance, and strength. Tg of the molded product is 60° C. or higher, preferably 70° C. or higher, and more preferably 80° C. or higher.

Furthermore, when a plant-derived material is used, it is possible to obtain molded products including a resin for an optical material which are in harmony with the global environment. The biomass ratio of the resin for an optical material can be set to 25% or higher.

From the viewpoint of utilizing non-fossil resources, it is preferable to use a material for which a plant-derived material is used and which has a high biomass ratio. However, as the biomass ratio of a resin is improved, there have been cases in which properties and the like degrade.

As a result of intensive studies, the present inventors found that, when an episulfide-containing composition that is obtained from glycerin obtained from plant-derived materials is used, a sulfide resin having a biomass ratio of 25% or higher and a molded product comprised of the resin can be obtained, contribution can be made to utilization of non-fossil resources, and furthermore, a resin for an optical material being excellent in terms of transparency, heat resistance, and strength and also having an excellent balance among properties such as refractive index, Abbe number, mold release properties, and the like and a molded product including the resin can be obtained and the present inventors completed the present invention.

[Uses]

Optical materials comprised of the molded product of the present embodiment can be provided with a variety of shapes by changing molds during casting polymerization. Specifically, the optical materials can be used in a variety of uses such as plastic lenses, camera lenses, light-emitting diodes (LEDs), prisms, optical fibers, information-recording substrates, filters, light-emitting diodes, optical lenses for vehicles, and optical lenses for robots. Particularly, the optical materials are preferred as optical materials such as plastic lenses, camera lenses, and light-emitting diodes or optical elements.

Examples of plastic lenses include plastic eyeglass lenses comprised of a polythiourethane resin and plastic polarizing lenses in which a layer comprised of a polythiourethane resin is laminated over at least one surface of a polarizing film.

[Process for producing plastic eyeglass lens] A method for manufacturing a plastic eyeglass lens of the present embodiment includes the following steps.

Step (1): The polymerizable composition for an optical material of the present embodiment is injected into a mold for lens casting.

Step (2): The polymerizable composition for an optical material is polymerization-cured in the mold for lens casting.

Hereinafter, the respective steps will be sequentially described.

Step (1)

In the present step, the polymerizable composition of the present embodiment is injected into a mold (a mold for lens casting) held using a gasket, tape, or the like. At this time, depending on properties necessary for molded products to be obtained, it is preferable to carry out a degassing treatment under reduced pressure, a filtration treatment such as pressurization or depressurization, or the like as necessary.

Step (2)

In the present step, the polymerization of the polymerizable composition casted in the mold is initiated at a predetermined temperature, and the composition is polymerized. Polymerization conditions significantly vary depending on the kinds of the polyisocyanate or alcohols being used, the shape of the mold, and the like and thus are not limited, and the composition is polymerized at a temperature of approximately 0° C. to 140° C. for 1 hour to 48 hours.

The obtained plastic eyeglass lens may be used after being provided with a coating layer (s) on one or both surface (s) as necessary. Examples of the coating layer include a primer layer, a hard coat layer, an antireflection layer, an antifogging coating layer, an antifouling layer, and a water-repellent layer. Each of these coating layers may be used singly, or a plurality of the coating layers may be used in a multilayer form. In a case in which the coating layers are provided on both surfaces, the same coating layers or different coating layers may be provided on the respective layers.

In these coating layers, an ultraviolet absorber for the purpose of protecting the lens or eyes from ultraviolet rays, an infrared absorber for the purpose of protecting eyes from infrared rays, a light stabilizer or an antioxidant for the purpose of improving the weather resistance of the lens, dyes or pigments and, furthermore, photochromic dyes or photochromic pigments for the purpose of enhancing the fashion properties of the lens, an antistatic agent, and, additionally, well-known additives for enhancing the performance of the lens may be jointly used. For layers coated by means of coating, a variety of levelling agents intended to improve coating properties may be used.

The primer layer is generally formed between a hard coat layer described below and an optical lens. The primer layer is a coating layer intended to improve adhesiveness to the hard coat layer and the lens which are formed on the primer layer and, in some cases, is also capable of improving impact resistance. Any material can be used for the primer layer as long as the material is highly adhesive to the obtained optical lens; generally, primer compositions including a urethane-based resin, an epoxy-based resin, a polyester-based resin, a melamine-based resin, and polyvinyl acetal as main components and the like are used. In the primer composition, an appropriate solvent having no influences on the lens may be used in order to adjust the viscosity of the composition. It is needless to say that no solvents may be used.

The primer layer can also be formed using any one of a coating method and a dry method. In a case in which a coating method is used, the primer layer is formed by applying the primer composition onto a lens using a well-known coating method such as spin coating or dip coating and then solidifying the primer composition. In a case in which a dry method is used, the primer layer is formed using a well-known dry method such as a CVD method or a vacuum deposition method. During the formation of the primer layer, the surface of the lens may be subjected to a pretreatment such as an alkali treatment, a plasma treatment, or an ultraviolet treatment as necessary in order to improve adhesiveness.

The hard coat layer is a coating layer intended to impart functions such as abrasion resistance, wear resistance, moisture resistance, hot water resistance, heat resistance, and weather resistance to the lens surface.

For the hard coat layer, generally, a hard coat composition including a curable organic silicon compound and one or more kinds of fine particles constituted of a complex oxide of one or more kinds of oxide fine particles of an element selected from an element group of Si, Al, Sn, Sb, Ta, Ce, La, Fe, Zn, W, Zr, In, and Ti and/or two or more kinds of elements selected from the above-described element group is used.

The hard coat composition preferably includes, in addition to the above-described components, at least any of amines, amino acids, metallic acetylacetonate complexes, organic acid metallic salts, perchloric acids, salts of perchloric acids, acids, metal chlorides, and polyfunctional epoxy compounds. In the hard coat composition, an appropriate solvent having no influences on the lens may be used. It is needless to say that the hard coat composition may include no solvents.

The hard coat layer is generally formed by applying the hard coat composition using a well-known coating method such as spin coating or dip coating and then curing the hard coat composition. Examples of a curing method include curing methods in which the hard coat composition is cured by means of thermal curing or irradiation with energy rays such as ultraviolet rays or visible light rays. In order to suppress the generation of interference fringes, the refractive index of the hard coat layer is preferably in a range of ±0.1 from the refractive index of the lens.

Generally, the antireflection layer is formed on the hard coat layer as necessary. Antireflection layers are classified into inorganic antireflection layers and organic antireflection layers, and, in a case in which the antireflection layer is an inorganic antireflection layer, the antireflection layer is formed using an inorganic oxide such as $SiO_2$ or $TiO_2$ and by a dry method such as a vacuum deposition method, a sputtering method, an ion plating method, an ion beam assist method, or a CVD method. In a case in which the antireflection layer is an organic antireflection layer, the antireflection layer is formed using a composition including an organic silicon compound and silica-based fine particles having internal voids and by a wet method.

The antireflection layer may have a single layer structure or a multilayer structure, and, in a case in which a single layer-structured antireflection layer is used, the refractive index of the antireflection layer is preferably lower than the refractive index of the hard coat layer by at least greater than or equal to 0.1. In order to effectively develop an antireflection function, a multilayered antireflection film is preferably formed, and, in this case, low-refractive index films and high-refractive index films are alternately laminated. In this case as well, the difference in the refractive index between the low-refractive index film and the high-refractive index film is preferably greater than or equal to 0.1. Examples of the high-refractive index films include films of ZnO, $TiO_2$, $CeO_2$, $Sb_2O_5$, $SnO_2$, $ZrO_2$, and $Ta_2O_5$, and examples of the low-refractive index films include $SiO_2$ films and the like.

On the antireflection layer, an antifogging coating layer, an antifouling layer, and a water-repellent layer may be formed as necessary. Regarding methods for forming the antifogging coating layer, the antifouling layer, and the water-repellent layer, treatment methods, treatment materials, and the like are not particularly limited as long as there are no adverse effects on the antireflection function, and well-known antifogging coating treatment methods, antifouling treatment methods, and water-repellent treatment methods, and materials can be used. Examples of antifogging coating and antifouling treatment methods include a method in which the surface is covered with a surfactant, a method in which a hydrophilic film is attached to the surface so as to impart water-absorbing properties, a method in which the surface is covered with fine protrusion and recesses so as to enhance water-absorbing properties, a method in which water-absorbing properties are imparted using a photocatalytic activity, a method in which a superhydrophobic treatment is carried out so as to prevent the attachment of water droplets, and the like. In addition, examples of the water-repellent treatment include a method in which a water-repellent treatment layer is formed by depositing or sputtering a fluorine-containing silane compound or the like, a method in which a fluorine-containing silane compound is dissolved in a solvent and then is applied, thereby forming a water-repellent treatment layer, and the like.

The plastic eyeglass lens of the present embodiment may be dyed using appropriate colorants in order to impart fashion properties or photochromic properties. The lens can be dyed using a well-known dyeing method and is dyed using, generally, the following method.

Generally, a lens raw material finished to a predetermined optical surface is immersed in a dyeing fluid in which a colorant being used is dissolved or uniformly dispersed (dyeing step), and then the colorant is fixed by heating the lens as necessary (post-dyeing annealing step). Colorants that are used in the dyeing step are not particularly limited as long as the colorants are well-known colorants; however, generally, oil-soluble dyes or dispersive dyes are used.

The solvent that is used in the dyeing step is not particularly limited as long as the solvent is capable of dissolving or uniformly dispersing colorants being used. In this dyeing step, a surfactant for dispersing the colorants in the dyeing fluid or a carrier for accelerating dyeing may be added as necessary. In the dyeing step, colorants and a surfactant, which is added as necessary, are dispersed in water or a mixture of water and an organic solvent so as to prepare a dyeing bath, an optical lens is immersed in this dyeing bath, and dyeing is carried out at a predetermined temperature for a predetermined time. The dyeing temperature and the dyeing time vary depending on desire coloration densities; however, generally, the dyeing temperature and the dyeing time are preferably 120° C. or lower and approximately several minutes to several tens of hours, and the dyeing density of the dyeing bath is in a range of 0.01% by weight to 10% by weight. In addition, in a case in which dyeing is difficult, the lens may be dyed under pressurization.

The post-dyeing annealing step which is carried out as necessary is a step in which a heating treatment is carried out on the dyed lens material. In the heating treatment, water remaining on the surface of the lens material dyed in the dyeing step is removed using a solvent or the like or the solvent is dried with wind, and then the lens material is retained in, for example, a furnace such as an infrared heating furnace in the atmosphere or a resistance heating furnace for a predetermined time. The post-dyeing annealing step prevents the discoloration of the dyed lens material (discoloration prevention step) and removes moisture that has intruded into the lens material during dyeing.

[Method for Manufacturing Plastic Polarizing Lens]

A method for manufacturing a plastic polarizing lens of the present embodiment includes the following steps.

Step (a): A polarizing film is fixed to the inside of a mold for lens casting in a state in which at least one surface of the polarizing film is separated from the mold.

Step (b): The polymerizable composition for an optical material of the present embodiment is injected into a space between the polarizing film and the mold.

Step (c): A layer comprised of a polythiourethane resin is laminated over at least one surface of the polarizing film by polymerization-curing the polymerizable composition for an optical material.

Hereinafter, the respective steps will be sequentially described.

Step (a)

A polarizing film comprised of a thermoplastic polyester is installed in the space of a mold for lens casting so that at least one of the film surfaces becomes parallel to the facing mold inner surface. A space is formed between the polarizing film and the mold. The polarizing film may be formed and attached in advance.

Step (b)

Next, in the space of the mold for lens casting, the polymerizable composition for an optical material of the present embodiment is injected into a space between the mold and the polarizing film using predetermined injection unit.

Step (c)

Next, the mold for lens casting to which the polarizing film is fixed into which the polymerizable composition for an optical material has been injected is heated in an oven or in a heatable device in water or the like using a predetermined temperature program for several hours to several tens of hours, thereby curing and shaping the polymerizable composition for an optical material.

Conditions of the temperature for the polymerization curing vary depending on the composition of the polymerizable composition, the kind of the catalyst, the shape of the mold, and the like and thus cannot be limited, and the polymerization curing is carried out at a temperature of 0° C. to 140° C. for 1 hour to 48 hours.

The product is removed from the mold for lens casting after the end of the curing and molding. Thereby, it is possible to obtain the plastic polarizing lens of the present embodiment in which a layer comprised of a polythiourethane resin is laminated over at least one surface of the polarizing film.

For the plastic polarizing lens of the present embodiment, for the purpose of alleviating strain caused by the polymerization, it is desirable to carry out an annealing treatment by heating the released lens.

The plastic polarizing lens of the present embodiment may be used after being provided with a coating layer(s) on one or both surface(s) as necessary. Examples of the coating layer, similar to the coating layer for the plastic eyeglass lens, include a primer layer, a hard coat layer, an antireflection layer, an antifogging coating layer, an antifouling layer, and a water-repellent layer.

Hitherto, the embodiment of the present invention has been described, but the embodiment is an example of the present invention, and a variety of other constitutions can be employed as long as the effects of the present invention are not impaired.

EXAMPLES

Hereinafter, the present invention will be described in more detail using examples, but the present invention is not limited thereto. In the following description, unless particularly otherwise described, "parts" and "%" are mass-based units.

(Method for Calculating the Biomass Ratio (%) of Episulfide Compound)

The carbon-based biomass ratio of epichlorohydrin which was a plant-derived material was considered as 100%, and the biomass ratio of the synthesized episulfide compound was calculated in terms of carbon on the basis of the above-described biomass ratio.

The biomass ratio (%) of the episulfide compound=
{(the number of carbon atoms derived from epichlorohydrin in the episulfide compound molecule)×(the biomass ratio (%) of epichlorohydrin)}/{(the number of carbon atoms in the episulfide compound molecule)}

(Method for Calculating the Biomass Ratio (%) of Polythiol)

The carbon-based biomass ratio of epichlorohydrin of a plant-derived material was considered as 100%, and the biomass ratio of the synthesized polythiol was calculated in terms of carbon on the basis of the above-described biomass ratio.

The biomass ratio (%) of polythiol={(the number of carbon atoms derived from epichlorohydrin in the polythiol molecule)×(the biomass ratio (%) of epichlorohydrin)}/{(the number of carbon atoms in the polythiol molecule)}

(Method for Calculating the Biomass Ratio (%) of Resin for Optical Material)

The biomass ratio of the resin described in Example 7 was calculated in terms of carbon on the basis of the biomass ratios of the episulfide compound and the polythiol.

(The biomass ratio (%) of the resin for an optical material)={(the number of carbon atoms in the episulfide compound used)×(the biomass ratio (%) of the episulfide compound)+(the number of carbon atoms in the polythiol compound used)×(the biomass ratio (%) of the polythiol compound)}/{(the number of carbon atoms in the episulfide compound used)+(the number of carbon atoms in the polythiol compound used)}

(Performance Test Method of Lens)

The lens obtained by means of polymerization was evaluated by carrying out a performance test. The performance test was carried out in terms of the refractive index, the Abbe number, the heat resistance, and the specific weight, and these were evaluated using the following test methods.

Refractive index (ne) and Abbe number (νe): The refractive index and the Abbe number were measured at 20° C. using a Pulfrich refractometer KPR-30 manufactured by Shimadzu Corporation.

Heat resistance: The glass transition temperature (Tg) in a TMA penetration method (with a load of 50 g and a pin tip diameter of 0.5 mmφ) was measured as the heat resistance using TMA-60 manufactured by Shimadzu Corporation.

Specific weight: Measured at 20° C. using the Archimedean method.

(GC-MS Measurement Conditions)

Epichlorohydrin or chloromercaptopropanol which was obtained by means of synthesis was analyzed by means of GC-MS.

GC-MS: HP-6890GC/5973N MSD
Column: DB-5MS
Oven conditions: 60° C. (1.0 min hold)→(10° C./min)–200° C. (5.0 min hold)
Carrier: He 1.5 ml/min

Example 1

Synthesis of 1,3-dichloro-2-propanol

Glycerin obtained from a plant-derived material (237 g, 2.57 mol), an aqueous solution of 33% hydrogen chloride (559.3 g, 5.06 mol), and adipic acid (219 g, 1.50 mol) were continuously supplied to a reactor (1) from different lines, and the retention time at 130° C. was operated to be 20 hours. During this reaction, vapor generated from the reactor (1) was supplied to a reactor (2) (25° C.), a water phase and an organic phase were supplied to a decanter (reactor (3)), the separated water-phase fraction was recycled to the reactor (2), and the reflux was held. A water phase including 15% of 1,3-dichloro-2-propanol and an organic phase including 88% of 1,3-dichloro-2-propanol were collected at the decanter outlet, thereby obtaining 1,3-dichloro-2-propanol (270 g, 2.09 mol).

Example 2

Synthesis of Epichlorohydrin 1,3-Dichloro-2-propanol obtained in Example 1 (258.76 g, 2.01 mol) was injected into a 1 liter reactor equipped with a glass thermostat. An aqueous solution of 19.1% by weight of NaOH (397.1 g, 1.90 mol) was added to a flask over 20 minutes under strong stirring at 25° C. At the end of the addition, the obtained mixture was transferred to a separating funnel. An organic phase was separated, and 99.97% epichlorohydrin (159.8 g, 1.73 mol) was obtained by means of distillation. The obtained epichlorohydrin was measured by means of GC-MS, and it was confirmed that the amounts of chlorine-based byproducts such as allyl chloride, 1,2-dichloropropane, 2,3-dichloropropene, 2-chloroallyl alcohol, 1,3-dichloropropene, and 1,2,3-trichloropropane were the detection limit (1 ppm) or lower and the contents thereof were smaller than the content of epichlorohydrin synthesized from a petroleum resource-derived raw material such as allyl chloride or propylene.

Example 3

Synthesis of Polythiol Compound

Synthesis of Polythiol Compound Including 4,8-dimercaptomethyl-1,11-dimercapto-3,6,9-trithiaundecane as Main Component 2-Mercaptoethanol (51.2 parts by weight), degassed water (dissolved oxygen level: 2 ppm) (26.5 parts by weight), and an aqueous solution of 49% by weight of sodium hydroxide (0.16 parts by weight) were injected into a reactor. Epichlorohydrin produced from plant-derived glycerin (EPICHLOROHYDRIN (ECH) manufactured by Nippon Solvay K. K.) (61.99 parts by weight) was added by dropping over 6.5 hours at 9° C. to 11° C. and, subsequently, was stirred for 60 minutes.

Next, an aqueous solution of 17.3% soda sulfide (150.0 parts by weight) was added by dropping over 5.5 hours at 7° C. to 37° C. and, subsequently, was stirred for 120 minutes.

In addition, 35.5% hydrochloric acid (279.0 parts by weight) was injected thereinto, then, thiourea having a purity of 99.90% (125.8 parts by weight) was injected thereinto, and the components were stirred for three hours under a reflux at 110° C., thereby causing a thiuronium chlorination reaction. After the cooling of the mixture to 45° C., toluene (214.0 parts by weight) was added thereto, the mixture was cooled to 26° C., an aqueous solution of 25% by weight of ammonia (206.2 parts by weight) was injected thereinto at 26° C. to 50° C. over 30 minutes, and the components were stirred at 50° C. to 65° C. for one hour so as to cause a hydrolysis reaction, thereby obtaining a toluene solution of the target polythiol compound. 36% Hydrochloric acid (59.4 parts by weight) was added to the toluene solution, and the mixture was washed with an acid at 34° C. to 39° C. for 30 minutes twice. Degassed water (dissolved oxygen level: 2 ppm) (118.7 parts by weight) was added thereto and was washed at 35° C. to 45° C. for 30 minutes five times. After the toluene and a small amount of moisture were removed under heating and depressurization, the mixture was filtered at reduced pressures using a 1.2 μm PTFE-type membrane filter, thereby obtaining a polythiol compound (115.9 parts by weight) including 4,8-dimercaptomethyl-1,11-dimercapto-3,6,9-trithiaundecane (hereinafter, Compound A), 4,7-dimercaptomethyl-1,11-dimercapto-3,6,9-trithiaundecane (hereinafter, Compound B), and 5,7-dimercaptomethyl-1,11-dimercapto-3,6,9-trithiaundecane (hereinafter, Compound C) as main components (an isomer mixture of Compounds A/B/C=85/5/10 (molar ratio)).

Example 4

Synthesis of Polythiol Compound

Synthesis of Polythiol Compound Including 4,8-dimercaptomethyl-1,11-dimercapto-3,6,9-trithiaundecane as Main Component 2-Mercaptoethanol (51.2 parts by weight), degassed water (dissolved oxygen level: 2 ppm) (26.5 parts by weight), and an aqueous solution of 49% by weight of sodium hydroxide (0.16 parts by weight) were injected into a reactor. 99.97% Epichlorohydrin obtained in Example 2 (1.99 parts by weight) was added by dropping over 6.5 hours at 9° C. to 11° C. and, subsequently, was stirred for 60 minutes.

Next, an aqueous solution of 17.3% soda sulfide (150.0 parts by weight) was added by dropping over 5.5 hours at 7° C. to 37° C. and, subsequently, was stirred for 120 minutes.

In addition, 35.5% hydrochloric acid (279.0 parts by weight) was injected thereinto, then, thiourea having a purity of 99.90% (125.8 parts by weight) was injected thereinto, and the components were stirred for three hours under a reflux at 110° C., thereby causing a thiuronium chlorination reaction. After the cooling of the mixture to 45° C., toluene (214.0 parts by weight) was added thereto, the mixture was cooled to 26° C., an aqueous solution of 25% by weight of ammonia (206.2 parts by weight) was injected thereinto at 26° C. to 50° C. over 30 minutes, and the components were stirred at 50° C. to 65° C. for one hour so as to cause a hydrolysis reaction, thereby obtaining a toluene solution of the target polythiol compound. 36% Hydrochloric acid (59.4 parts by weight) was added to the toluene solution, and the mixture was washed with an acid at 34° C. to 40° C. for 30 minutes twice. Degassed water (dissolved oxygen level: 2 ppm) (118.7 parts by weight) was added thereto and was washed at 35° C. to 45° C. for 30 minutes five times. After the toluene and a small amount of moisture were removed under heating and depressurization, the mixture was filtered at reduced pressures using a 1.2 μm PTFE-type membrane filter, thereby obtaining a polythiol compound (116.1 parts by weight) including 4,8-dimercaptomethyl-1,11-dimercapto-3,6,9-trithiaundecane (hereinafter, Compound A), 4,7-dimercaptomethyl-1,11-dimercapto-3,6,9-trithiaundecane (hereinafter, Compound B), and 5,7-dimercaptomethyl-1,11-dimercapto-3,6,9-trithiaundecane (hereinafter, Compound C) as main components (an isomer mixture of Compounds A/B/C=85/5/10 (molar ratio)).

The biomass ratio of the polythiol compound is calculated using the following equation in terms of carbon on the basis of the biomass ratio of epichlorohydrin of 100%.

The biomass ratio of the polythiol compound={(the number of carbon atoms derived from epichlorohydrin in the polythiol compound molecule)× (the biomass ratio (%) of epichlorohydrin)}/ {(the number of carbon atoms in the polythiol compound molecule)}=60%

Example 5

Synthesis of Episulfide Compound

Epichlorohydrin produced from plant-derived glycerin (EPICHLOROHYDRIN(ECH)) manufactured by Nippon Solvay K. K.) (190 g (2 mol)), methanol (500 ml), and calcium hydroxide (1.0 g) were injected in a reaction flask equipped with a stirring rod, a thermometer, a gas sealing tube, and a condenser, the inside temperature was held in a range of 0° C. to 5° C. under stirring, hydrogen sulfide gas (75 g, 2.2 mol) was blown into the reaction system through the gas sealing tube over two hours, and the components were aged at 5° C. for three hours.

The reaction liquid was filtered, methanol was removed, and then the residue was distilled away, thereby obtaining chloromercaptopropanol. In the obtained chloromercaptopropanol, pure water (1,000 ml), and sodium hydrogen carbonate (168 g, 2 mol) were injected, solid iodine (254 g, 1 mol) was injected in a split manner over one hour while holding the inside temperature in a range of 5° C. to 10° C., and the components were aged at 10° C. for 12 hours.

The reaction liquid that had been aged was filtered, and the obtained white crystals were dried at reduced pressure. The dried white crystals, methanol (250 ml), and toluene (500 ml) were again injected in the reactor, 47 wt % sodium hydroxide (240 g, 2.8 mol) was added dropwise for one hour while holding the inside temperature in a range of 3° C. to 5° C., and the components were aged for 30 minutes. After the end of the reaction, toluene (100 ml) was added thereto, and the organic layer was washed with pure water three times.

The obtained organic layer is dehydrated with anhydrous magnesium sulfate and then is filtrated, and solvent was removed from the obtained filtrate.

After removing solvent, the residual was filtered, and bis(2,3-epoxypropyl) disulfide was obtained (yield: 92%). Bis(2,3-epoxypropyl) disulfide (100 g, 0.54 mol), thiourea (100 g, 1.3 mol), acetic acid (2 g), toluene (250 ml), and methanol (200 ml) were injected in a reaction flask equipped with a stirrer, a thermometer, and a condenser, the inside temperature was held at 15° C., and the components were stirred for 16 hours.

After the end of the reaction, toluene (150 ml) was added thereto, and the mixture was washed with sodium chloride solution, 1% sulfuric acid water, and, again, sodium chloride solution. The obtained organic layer is dehydrated with anhydrous magnesium sulfate and then is filtrated, and solvent was removed from the obtained filtrate. Acetonitrile (600 ml) was added to residue obtained by removing solvent to dissolve it, and the supernatant solution was filtered.

The residue obtained by removing solvent from the obtained filtrate was filtered, thereby obtaining a composition (77.5 g) (the purity-equivalent yield was 58%) of a thioepoxy compound containing 85 wt % of bis(2,3-epithiopropyl) disulfide. This composition (50 g) of a thioepoxy compound having a purity of 85 wt % was sorted by means of silica gel column chromatography, thereby obtaining an episulfide compound (38 g).

Example 6

Synthesis of Episulfide Compound 99.97% Epichlorohydrin obtained in Example 2 (190 g (2 mol)), methanol (500 ml), and calcium hydroxide (1.0 g) were injected in a reaction flask equipped with a stirring rod, a thermometer, a gas sealing tube, and a condenser, the inside temperature was held in a range of 0° C. to 5° C. under stirring, hydrogen sulfide gas (75 g, 2.2 mol) was blown into the reaction system through the gas sealing tube over two hours, and the components were aged at 5° C. for three hours.

The reaction liquid was filtered, methanol was removed from a filtrate, and then the residue was distilled away, thereby obtaining chloromercaptopropanol. In chloromercaptopropanol obtained from epichlorohydrin synthesized from a petroleum resource-derived raw material such as allyl chloride or propylene (manufactured by Asahi Gosei Kagaku Co., Ltd.), the component having 10 minutes of a retention time in GC-MS measurement was 0.2% in terms of the strength ratio. In contrast, the component having 10 minutes of a retention time in the chloromercaptopropanol obtained herein was 0.03% in terms of the strength ratio. It became clear that, when epichlorohydrin produced from glycerin was used as a raw material, the generation of impurities derived from chlorine-based impurities was suppressed, and the content of impurities could be suppressed.

The obtained chloromercaptopropanol, pure water (1,000 ml), and sodium hydrogen carbonate (168 g, 2 mol) were injected, solid iodine (254 g, 1 mol) was injected in a split manner over one hour while holding the inside temperature in a range of 5° C. to 10° C., and the components were aged at 10° C. for 12 hours.

The reaction liquid that had been aged was filtered, and the obtained white crystals were dried at reduced pressure. The dried white crystals, methanol (250 ml), and toluene (500 ml) were again injected in the reactor, 47 wt % caustic soda (240 g, 2.8 mol) was added dropwise for one hour while holding the inside temperature in a range of 3° C. to 5° C., and the components were aged for 30 minutes. After the end of the reaction, toluene (100 ml) was added thereto, and the organic layer was washed with pure water three times.

The obtained organic layer is dehydrated with anhydrous magnesium sulfate and then is filtrated, and solvent was removed from the obtained filtrate.

After removing solvent, the residual was filtered, and bis(2,3-epoxypropyl) disulfide was obtained (yield: 920). Bis(2,3-epoxypropyl) disulfide) (100 g, 0.54 mol), thiourea (100 g, 1.3 mol), acetic acid (2 g), toluene (250 ml), and methanol (200 ml) were injected in a reaction flask equipped with a stirrer, a thermometer, and a condenser, the inside temperature was held at 15° C., and the components were stirred for 16 hours.

After the end of the reaction, toluene (150 ml) was added thereto, and the mixture was washed with sodium chloride solution, 1% sulfuric acid water, and, again, sodium chloride solution. The obtained organic layer is dehydrated with anhydrous magnesium sulfate and then is filtrated, and solvent was removed from the obtained filtrate. Acetonitrile (600 ml) was added to residue obtained by removing solvent to dissolve it, and the supernatant solution was filtered. The residue obtained by removing solvent from a filtrate was filtered, thereby obtaining a composition (77.9 g) (the purity-equivalent yield was 58%) of a thioepoxy compound containing 85 wt % of bis(2,3-epithiopropyl) disulfide. This composition (50 g) of a thioepoxy compound having a purity of 85 wt % was sorted by means of silica gel column chromatography, thereby obtaining an episulfide compound (39 g).

The biomass ratio of the episulfide compound is calculated using the following equation in terms of carbon on the basis of the biomass ratio of epichlorohydrin of 100%.

The biomass ratio of the episulfide compound={(the number of carbon atoms derived from epichlorohydrin in the episulfide compound molecule)× (the biomass ratio (%) of epichlorohydrin)}/ {(the number of carbon atoms in the episulfide compound molecule)}=100%

Example 7

N,N-dimethylcyclohexylamine (0.007 g) and N,N-dicyclohexylmethylamine (0.032 g) were dissolved in bis(2,3-epithiopropyl) disulfide (the episulfide compound obtained in Example 5; 31.8 g), and a mixture (the polythiol compound obtained in Example 3; 3.2 g) including 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane as main components was added thereto, and the components were stirred at 20° C. for 30 minutes, thereby preparing a blended liquid. This blended liquid was degassed at 600 Pa for one hour, was filtered using a 1 μm PTFE filter, and then was injected into a glass mold for 2C plano lense having a central thickness of 2 mm and a diameter of 80 mm. This glass mold was heated little by little from 30° C. to 80° C. for 19 hours and was held at 80° C. for two hours. The mold was cooled to room temperature and was removed from the glass mold, thereby obtaining a resin lens. The obtained resin lens was further annealed at 120° C. for three hours. The obtained resin had a refractive index (ne) of 1.738, an Abbe number of 32, a Tg of 78° C., a specific weight of 1.47, and a biomass ratio of 96%.

Example 8

N,N-dimethylcyclohexylamine (0.007 g) and N,N-dicyclohexylmethylamine (0.032 g) were dissolved in bis(2,3-epithiopropyl) disulfide (the episulfide compound obtained in Example 6; 31.8 g), and a mixture (the polythiol compound obtained in Example 4; 3.2 g) including 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane as main components was added thereto, and the components were stirred at 20° C. for 30 minutes, thereby preparing a blended liquid. This blended liquid was degassed at 600 Pa for one hour, was filtered using a 1 μm PTFE filter, and then was injected into a glass mold for 2C plano lense having a central thickness of 2 mm and a diameter of 80 mm. This glass mold was heated little by little from 30° C. to 80° C. for 19 hours and was held at 80° C. for two hours. The mold was cooled to room temperature and was removed from the glass mold, thereby obtaining a resin lens. The obtained resin lens was further annealed at 120° C. for three hours. The obtained resin had a refractive index (ne) of 1.738, an Abbe number of 32, a Tg of 78° C., a specific weight of 1.47, and a biomass ratio of 96%.

The biomass ratio (%) of the resin=[{31.8 (parts by weight of the episulfide compound)/210.4 (the molecular weight of the episulfide compound)×6 (the number of carbon atoms in one episulfide compound molecule)×100 (the biomass ratio (%) of the episulfide compound)}+ {3.2 (parts by weight of the polythiol compound)/366.7 (the molecular weight of the polythiol compound)×10 (the number of carbon atoms in one polythiol compound molecule)×60 (the biomass ratio (%) of the polythiol compound)}]/[{31.8 (parts by weight of the episulfide compound)/210.4 (the molecular weight of the episulfide compound)×6 (the number of carbon atoms in one episulfide compound molecule)}+{3.2 (parts by weight of the polythiol compound)/366.7 (the molecular weight of the polythiol compound)×10 (the number of carbon atoms in one polythiol compound molecule)}]/ =96%

In the above-described examples, it was possible to obtain sulfide-based resins for optical materials having an excellent balance of properties such as high refractive index and high heat resistance from polymerizable compositions including an episulfide compound that was obtained using a raw material obtained from glycerin, and it was possible to obtain resins for optical materials having a high biomass ratio of 70% or higher by combining an episulfide compound, a polythiol compound, and a compound produced from a plant-derived material.

The present application claims priority on the basis of Japanese Patent Application No. 2014-047890 filed on Mar. 11, 2014 and Japanese Patent Application No. 2014-185995 filed on Sep. 12, 2014, the contents of which are incorporated herein.

The invention claimed is:

1. A process for producing an episulfide compound for an optical material, comprising:
   a step of chlorinating glycerin to obtain dichloropropanol;
   a step of epoxidizing the dichloropropanol to obtain epichlorohydrin;
   a step of reacting the epichlorohydrin with a sulfating agent to obtain a bis(chlorohydrin) (di)sulfide compound through a thiol compound;
   a step of epoxidizing the bis(chlorohydrin) (di)sulfide compound under basic conditions to obtain an epoxy compound; and
   a step of reacting the epoxy compound with a sulfating agent to obtain an episulfide compound represented by following General Formula (1):

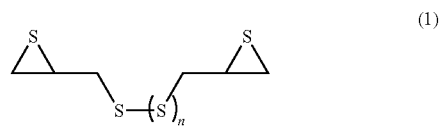

wherein, in the formula, n represents 0 or 1,
wherein the step of chlorinating glycerin is a step of chlorinating glycerin to obtain a composition containing dichloropropanol and chlorine-based byproduct which is at least one compound selected from allyl chloride, 1,2-dichloropropane, 2,3-dichloropropene, 2-chloroallyl alcohol, 1,3-dichloropropene, and 1,2,3-trichloropropane, and
wherein the step of epoxidizing the dichloropropanol is a step of epoxidizing the dichloropropanol of the composition to obtain a composition containing epichlorohydrin and 5,000 ppm or less of the chlorine-based byproduct.

2. The process for producing an episulfide compound for an optical material according to claim 1,
   wherein the glycerin is obtained from plant-derived materials.

3. A process for producing an episulfide-containing composition, comprising:
   a step of chlorinating glycerin in a composition a including the glycerin obtained from plant-derived materials to obtain a composition b including dichloropropanol;
   a step of epoxidizing the dichloropropanol in the composition b to obtain a composition c including epichlorohydrin;
   a step of reacting the epichlorohydrin with a sulfating agent in the composition c to obtain a composition d including a bis(chlorohydrin) (di)sulfide compound through a thiol compound;
   a step of epoxidizing the bis(chlorohydrin) (di)sulfide compound under basic conditions in the composition d to obtain a composition e including an epoxy compound; and
   a step of reacting the epoxy compound with a sulfating agent in the composition e to obtain a composition f including an episulfide represented by following General Formula (1):

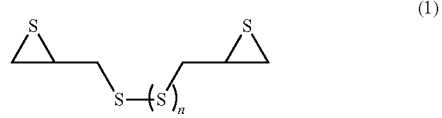

wherein, in the formula, n represents 0 or 1,
wherein the step of chlorinating glycerin in a composition a including the glycerin is a step of chlorinating glycerin to obtain a composition b containing dichloropropanol and chlorine-based byproduct which is at least one compound selected from allyl chloride, 1,2-dichloropropane, 2,3-dichloropropene, 2-chloroallyl alcohol, 1,3-dichloropropene, and 1,2,3-trichloropropane, and
wherein the step of epoxidizing the dichloropropanol in the composition b is a step of epoxidizing the dichloropropanol in the composition b to obtain a composition c containing epichlorohydrin and 5,000 ppm or less of the chlorine-based byproduct.

* * * * *